United States Patent
Fletcher et al.

(10) Patent No.: US 10,420,801 B2
(45) Date of Patent: Sep. 24, 2019

(54) ISOLATION AND USE OF HUMAN LYMPHOID ORGAN-DERIVED SUPPRESSIVE STROMAL CELLS

(71) Applicants: Dana-Farber Cancer Institute, Inc., Boston, MA (US); The General Hospital Corporation, Boston, MA (US)

(72) Inventors: Anne Fletcher, Oakleigh South (AU); Shannon J. Turley, West Roxbury, MA (US); Biju Parekkadan, Cambridge, MA (US)

(73) Assignees: The General Hospital Corporation, Boston, MA (US); Dana-Farber Cancer Institute, Inc., Boston, MA (US)

( * ) Notice: Subject to any disclaimer, the term of this patent is extended or adjusted under 35 U.S.C. 154(b) by 862 days.

(21) Appl. No.: 14/386,535

(22) PCT Filed: Mar. 13, 2013

(86) PCT No.: PCT/US2013/030802
§ 371 (c)(1),
(2) Date: Sep. 19, 2014

(87) PCT Pub. No.: WO2013/142186
PCT Pub. Date: Sep. 26, 2013

(65) Prior Publication Data
US 2015/0050298 A1 Feb. 19, 2015

Related U.S. Application Data

(60) Provisional application No. 61/613,697, filed on Mar. 21, 2012.

(51) Int. Cl.
| | |
|---|---|
| *A61K 35/26* | (2015.01) |
| *C12N 5/078* | (2010.01) |
| *C12N 5/077* | (2010.01) |
| *A61K 38/18* | (2006.01) |
| *A61K 38/19* | (2006.01) |
| *A61K 38/20* | (2006.01) |
| *A61K 35/12* | (2015.01) |

(52) U.S. Cl.
CPC ............ *A61K 35/26* (2013.01); *C12N 5/0651* (2013.01); *C12N 5/0669* (2013.01); *A61K 38/1866* (2013.01); *A61K 38/19* (2013.01); *A61K 38/204* (2013.01); *A61K 2035/122* (2013.01)

(58) Field of Classification Search
None
See application file for complete search history.

(56) References Cited

U.S. PATENT DOCUMENTS

| | | | |
|---|---|---|---|
| 2004/0047873 A1* | 3/2004 | Al-Shamkhani | C07K 14/70575 424/185.1 |
| 2007/0027543 A1 | 2/2007 | Gimble et al. | |
| 2010/0055076 A1 | 3/2010 | Lim et al. | |
| 2010/0178700 A1 | 7/2010 | Fletcher et al. | |
| 2014/0369970 A1* | 12/2014 | Alfonso | A61K 35/28 424/93.7 |
| 2015/0086584 A1* | 3/2015 | Gilboa | A61K 47/549 424/192.1 |

FOREIGN PATENT DOCUMENTS

| | | |
|---|---|---|
| JP | 2003/530124 A | 10/2003 |
| JP | 2004/041195 A | 2/2004 |
| JP | 2009/507527 A | 2/2009 |
| JP | 2009/273444 A | 11/2009 |
| WO | WO2001030802 * | 5/2001 |
| WO | WO 01/77169 A2 | 10/2001 |
| WO | WO 03/105874 A1 | 12/2003 |
| WO | WO 2011/005326 A1 | 1/2011 |

OTHER PUBLICATIONS

Schulze-Koops, Lymphopenia and autoimmune diseases. Arthritis Res Ther. 2004;6(4):178-80. Epub Jun. 22, 2004.
International Search Report and Written Opinion for PCT/US2013/030802 dated May 17, 2013.
International Preliminary Report on Patentability for PCT/US2013/030802 dated Oct. 2, 2014.
Ahrendt et al., Stromal cells confer lymph node-specific properties by shaping a unique microenvironment influencing local immune responses. J Immunol. Aug. 1, 2008;181(3):1898-907.
Ansel et al., A chemokine-driven positive feedback loop organizes lymphoid follicles. Nature. Jul. 20, 2000;406(6793):309-14.
Bajénoff et al., Stromal cell networks regulate lymphocyte entry, migration, and territoriality in lymph nodes. Immunity. Dec. 2006;25(6):989-1001. Epub Nov. 16, 2006.
Buettner et al., Lymph node stromal cells strongly influence immune response suppression. Eur J Immunol. Mar. 2011;41(3):624-33. doi:10.1002/eji.201040681. Epub Jan. 18, 2011.
Cao et al., Phospholipid transfer protein is regulated by liver X receptors in vivo. J Biol Chem. Oct. 18, 2002;277(42):39561-5. Epub Aug. 9, 2002.
Chyou et al., Fibroblast-type reticular stromal cells regulate the lymph node vasculature. J Immunol. Sep. 15, 2008;181(6):3887-96.

(Continued)

*Primary Examiner* — Michail A Belyavskyi
(74) *Attorney, Agent, or Firm* — Wolf, Greenfield & Sacks, P.C.

(57) ABSTRACT

A method for suppressing an immune response is provided. The method involves administration of isolated lymphoid tissue-derived suppressive stromal cells (LSSC) to a subject in need of such treatment in an amount effective to suppress the immune response in the subject. The invention also involves a method to isolate LSSC by digesting lymphoid tissue fragments using a combination of an enzyme mix and agitation and then collecting the LSSC. Pharmaceutical preparations comprising LSSC are also provided.

20 Claims, 17 Drawing Sheets

(56) References Cited

OTHER PUBLICATIONS

Cohen et al., Lymph node-resident lymphatic endothelial cells mediate peripheral tolerance via Aire-independent direct antigen presentation. J Exp Med. Apr. 12, 2010;207(4):681-8. doi:10.1084/jem.20092465. Epub Mar. 22, 2010.

Coles et al., Cellular and molecular requirements in lymph node and Peyer's patch development. Prog Mol Biol Transl Sci. 2010;92:177-205. doi: 10.1016/S1877-1173(10)92008-5.

Cupedo et al., Presumptive lymph node organizers are differentially represented in developing mesenteric and peripheral nodes. J Immunol. Sep. 1, 2004;173(5):2968-75.

Cyster et al., Follicular stromal cells and lymphocyte homing to follicles. Immunol Rev. Aug. 2000;176:181-93.

Dinarello, Biologic basis for interleukin-1 in disease. Blood. Mar. 15, 1996;87(6):2095-147.

Eikelenboom et al., The histogenesis of lymph nodes in rat and rabbit. Anat Rec. Feb. 1978;190(2):201-15.

English et al., IFN-gamma and TNF-alpha differentially regulate immunomodulation by murine mesenchymal stem cells. Immunol Lett. Jun. 15, 2007;110(2):91-100. Epub Apr. 26, 2007.

Fletcher et al., Lymph node fibroblastic reticular cells directly present peripheral tissue antigen under steady-state and inflammatory conditions. J Exp Med. Apr. 12, 2010;207(4):689-97. doi:10.1084/jem.20092642. Epub Mar. 22, 2010.

Fletcher et al., Lymph node stroma broaden the peripheral tolerance paradigm. Trends Immunol. Jan. 2011;32(1):12-8. doi:10.1016/j.it.2010.11.002. Epub Dec. 10, 2010.

Fletcher et al., Reproducible isolation of lymph node stromal cells reveals site-dependent differences in fibroblastic reticular cells. Front Immunol. Sep. 12, 2011;2:35. doi:10.3389/fimmu.2011.00035. eCollection 2011.

Galdones et al., Role of retinoic acid receptors alpha1 and gamma in the response of murine limbs to retinol in vitro. Birth Defects Res A Clin Mol Teratol. Jan. 2006;76(1):39-45.

Gallucci et al., IL-6 modulates alpha-smooth muscle actin expression in dermal fibroblasts from IL-6-deficient mice. J Invest Dermatol. Mar. 2006;126(3):561-8.

Gardner et al., Deletional tolerance mediated by extrathymic Aire-expressing cells. Science. Aug. 8, 2008;321(5890):843-7. doi:10.1126/science.1159407.

Hadis et al., Intestinal tolerance requires gut homing and expansion of FoxP3+ regulatory T cells in the lamina propria. Immunity. Feb. 25, 2011;34(2):237-46. doi: 10.1016/j.immuni.2011.01.016. Epub Feb. 17, 2011.

Hu et al., Activation of PDGF receptor alpha in vascular smooth muscle cells by mechanical stress. FASEB J. Sep. 1998;12(12):1135-42.

Iwata, Retinoic acid production by intestinal dendritic cells and its role in T-cell trafficking. Semin Immunol. Feb. 2009;21(1):8-13. doi:10.1016/j.smim.2008.09.002. Epub Oct. 11, 2008.

Junt et al., Form follows function: lymphoid tissue microarchitecture in antimicrobial immune defence. Nat Rev Immunol. Oct. 2008;8(10):764-75. doi:10.1038/nri2414.

Katakai et al., A novel reticular stromal structure in lymph node cortex: an immuno-platform for interactions among dendritic cells, T cells and B cells. Int Immunol. Aug. 2004;16(8):1133-42. Epub Jul. 5, 2004.

Katakai et al., Lymph node fibroblastic reticular cells construct the stromal reticulum via contact with lymphocytes. J Exp Med. Sep. 20, 2004;200(6):783-95.

Katakai et al., Organizer-like reticular stromal cell layer common to adult secondary lymphoid organs. J Immunol. Nov. 1, 2008;181(9):6189-200.

Koni et al., Distinct roles in lymphoid organogenesis for lymphotoxins alpha and beta revealed in lymphotoxin beta-deficient mice. Immunity. Apr. 1997;6(4):491-500.

Lee et al., Peripheral antigen display by lymph node stroma promotes T cell tolerance to intestinal self. Nat Immunol. Feb. 2007;8(2):181-90. Epub Dec. 31, 2006.

Link et al., Association of T-zone reticular networks and conduits with ectopic lymphoid tissues in mice and humans. Am J Pathol. Apr. 2011;178(4):1662-75. doi:10.1016/j.ajpath.2010.12.039.

Link et al., Fibroblastic reticular cells in lymph nodes regulate the homeostasis of naive T cells. Nat Immunol. Nov. 2007;8(11):1255-65. Epub Sep. 23, 2007.

Luther et al., Coexpression deletion of the chemokines ELC and SLC by T zone stromal cells and deletion of the ELC gene in the plt/plt mouse. Proc Natl Acad Sci U S A. Nov. 7, 2000;97(23):12694-9.

MacKay et al., Cracking the BAFF code. Nat Rev Immunol. Jul. 2009;9(7):491-502. doi: 10.1038/nri2572.

Magnusson et al., Direct presentation of antigen by lymph node stromal cells protects against CD8 T-cell-mediated intestinal autoimmunity. Gastroenterology. Apr. 2008;134(4):1028-37. doi: 10.1053/j.gastro.2008.01.070. Epub Jan. 30, 2008.

Matsuura et al., Regulation of hepatic lecithin: retinol acyltransferase activity by retinoic acid. Arch Biochem Biophys. Mar. 1993;301(2):221-7.

Mebius, Organogenesis of lymphoid tissues. Nat Rev Immunol. Apr. 2003;3(4):292-303. Review. Erratum in: Nat Rev Immunol. Jun. 2003;3(6):509.

Mei et al., Mesenchymal stem cells reduce inflammation while enhancing bacterial clearance and improving survival in sepsis. Am J Respir Crit Care Med. Oct. 15, 2010;182(8):1047-57. doi:10.1164/rccm.201001-00100C. Epub Jun. 17, 2010.

Müller et al., Review: The chemokine receptor CXCR3 and its ligands CXCL9, CXCL10 and CXCL11 in neuroimmunity—a tale of conflict and conundrum. Neuropathol Appl Neurobiol. Aug. 2010;36(5):368-87. doi:10.1111/j.1365-2990.2010.01089.x. Epub May 6, 2010.

Németh et al., Bone marrow stromal cells attenuate sepsis via prostaglandin E(2)-dependent reprogramming of host macrophages to increase their interleukin-10 production. Nat Med. Jan. 2009;15(1):42-9. doi: 10.1038/nm.1905. Epub Nov. 21, 2008. Erratum in: Nat Med. Apr. 2009;15(4):462.

Nichols et al., Deletional self-tolerance to a melanocyte/melanoma antigen derived from tyrosinase is mediated by a radio-resistant cell in peripheral and mesenteric lymph nodes. J Immunol. Jul. 15, 2007;179(2):993-1003.

Ohtani et al., Abundant expression of CXCL9 (MIG) by stromal cells that include dendritic cells and accumulation of CXCR3+ T cells in lymphocyte-rich gastric carcinoma. J Pathol. Jan. 2009;217(1):21-31. doi: 10.1002/path.2448.

Pabst et al., NKX2.3 is required for MAdCAM-1 expression and homing of lymphocytes in spleen and mucosa-associated lymphoid tissue. EMBO J. May 2, 2000;19(9):2015-23.

Panuncio et al., Adrenergic innervation in reactive human lymph nodes. J Anat. Jan. 1999;194 (Pt 1):143-6.

Pedersen, The anti-inflammatory effect of exercise: its role in diabetes and cardiovascular disease control. Essays Biochem. 2006;42:105-17.

Rébé et al., Induction of transglutaminase 2 by a liver X receptor/retinoic acid receptor alpha pathway increases the clearance of apoptotic cells by human macrophages. Circ Res. Aug. 14, 2009;105(4):393-401. doi: 10.1161/CIRCRESAHA.109.201855. Epub Jul. 23, 2009.

Scandella et al., Restoration of lymphoid organ integrity through the interaction of lymphoid tissue-inducer cells with stroma of the T cell zone. Nat Immunol. Jun. 2008;9(6):667-75. doi:10.1038/ni.1605. Epub Apr. 20, 2008.

Sixt et al., The conduit system transports soluble antigens from the afferent lymph to resident dendritic cells in the T cell area of the lymph node. Immunity. Jan. 2005;22(1):19-29.

Warnock et al., Molecular mechanisms of lymphocyte homing to peripheral lymph nodes. J Exp Med. Jan. 19, 1998;187(2):205-16.

Willard-Mack, Normal structure, function, and histology of lymph nodes. Toxicol Pathol. 2006;34(5):409-24.

(56) References Cited

OTHER PUBLICATIONS

Woolf et al., Lymph node chemokines promote sustained T lymphocyte motility without triggering stable integrin adhesiveness in the absence of shear forces. Nat Immunol. Oct. 2007;8(10):1076-85. Epub Aug. 26, 2007.
Yip et al., Deaf1 isoforms control the expression of genes encoding peripheral tissue antigens in the pancreatic lymph nodes during type 1diabetes. Nat Immunol. Sep. 2009;10(9):1026-33. doi:10.1038/ni.1773. Epub Aug. 9, 2009.
Yoneyama et al., Pivotal role of dendritic cell-derived CXCL10 in the retention of T helper cell 1 lymphocytes in secondary lymph nodes. J Exp Med. May 20, 2002;195(10):1257-66.
Zampetaki et al., Biomechanical stress induces IL-6 expression in smooth muscle cells via Ras/Rac 1-p38 MAPK-NF-kappaB signaling pathways. Am J Physiol Heart Circ Physiol. Jun. 2005;288(6):H2946-54. Epub Jan. 28, 2005.
Extended European Search Report for EP 13764099.1 dated Oct. 7, 2015.
Fitzgerald et al., Immune suppression of human lymphoid tissues and cells in rotating suspension culture and onboard the International Space Station. In Vitro Cell Dev Biol Anim. Dec. 2009;45(10):622-32. doi: 10.1007/s11626-009-9225-2.
Malhotra et al., Stromal and hematopoietic cells in secondary lymphoid organs: partners in immunity. Immunol Rev. Jan. 2013;251(1):160-76. doi: 10.1111/imr.12023.
Malhotra et al., Transcriptional profiling of stroma from inflamed and resting lymph nodes defines immunological hallmarks. Nat Immunol. Apr. 1, 2012;13(5):499-510. doi: 10.1038/ni.2262.

\* cited by examiner

Schematic diagram of pooled murine lymph node stromal cell digestion and preparation for cell sorting Validation of a low-mortality method for isolation of lymph node stromal subsets Site-specific transcriptional upregulation of cytokines in FRCs from skin-draining lymph nodes Three-dimensional (3D) culture of FRCs mimics *in vitro* function Lymphoid tissue-derived suppressor cells suppress the proliferation of activated allogeneic splenocytes LSSCs suppress the proliferation of activated, xenogeneic T cells LSSCs suppress T cell proliferation via novel mechanisms Two major subpopulations of lymphoid tissue-derived suppressor cells each suppress the
proliferation of activated allogeneic T cells LSSCs halt the division of pre-activated allogeneic T cells LSSCs significantly reduce early lethality in mice with severe graft-versus-host disease Morphological characteristics of LSSC Ex vivo expanded mouse lymph node stroma reduce the lethality of acute septic shock

ISOLATION AND USE OF HUMAN LYMPHOID ORGAN-DERIVED SUPPRESSIVE STROMAL CELLS

RELATED APPLICATIONS

This application is a national stage filing under 35 U.S.C. § 371 of international application PCT/US2013/030802, filed Mar. 13, 2013, which was published under PCT Article 21(2) in English, which claims the benefit under 35 U.S.C. § 119(e) of U.S. provisional application Ser. No. 61/613,697, filed Mar. 21, 2012, the content of which each referenced application is incorporated by reference herein in its entirety.

FEDERALLY SPONSORED RESEARCH

This invention was made with Government support under NIH Grant DK074500, K01DK087770, and AI045757. Accordingly, the Government has certain rights in this invention.

FEDERALLY SPONSORED RESEARCH

This invention was made with government support under grant number AI037562 awarded by the National Institutes of Health. The government has certain rights in the invention.

BACKGROUND OF THE INVENTION

Immunosuppressive drugs are used to inhibit or prevent the activity of the immune system for the treatment of certain diseases. Clinically, they are used to treat or prevent a number of conditions, for example, to prevent the rejection of transplanted organs and tissues (e.g. bone marrow, heart, kidney, liver etc.), and in the treatment of inflammatory diseases or autoimmune diseases, such as rheumatoid arthritis, multiple sclerosis, psoriasis, and inflammatory bowel disease. Immunosuppressive drugs currently approved for treatment of chronic inflammatory diseases need to be frequently administered, and carry significant side effects including risks of renal toxicity and morbidity.

Although immunosuppressive stromal cell types have been described (e.g. mesenchymal stromal cells), they are poorly defined, and have failed to meet primary efficacy endpoints in clinical trials. In addition, isolation of stromal cells remains challenging due to difficulties in successfully isolating these cells. Due to the severity and breath of conditions caused by unwanted immune activity, such as autoimmune or inflammatory diseases, there is a great need for developing effective treatments of such diseases.

SUMMARY OF THE INVENTION

The invention, relates in some aspects, to the discovery that stromal cells isolated from lymph nodes can suppress an immune response. The ability of lymph node-derived stromal cells to suppress an immune response combined with their known ability to attract immune cells makes them an effective tool to suppress an immune response in a subject. Accordingly, some aspects of the invention involve a method for suppressing an immune response by administering to a subject in need of such treatment isolated lymphoid tissue-derived suppressive stromal cells (LSSC) in an amount effective to suppress the immune response in the subject. In some embodiments, the LSSC that are administered to the subject are ex vivo expanded cells. In some embodiments, the LSSC that are administered to the subject are substantially free of non-LSSC. In some embodiments, at least 0.1 million LSSC/kg are administered to the subject. In some embodiments, at least 1 million LSSC/kg are administered to the subject.

The LSSC may be obtained from any one or combination of the following tissues: lymph nodes, spleen, thymus, tonsils, adenoids, and Peyer's patches. The LSSC may be autologous, allogeneic or xenogeneic with respect to the subject.

In some embodiments, the LSSC are on or in a two or three dimensional framework implanted into the subject. In some embodiments, the LSSC are administered to the subject by intravenous, intraperitoneal, intra-arterial, subcutaneous, or intramuscular injection or by local administration into a lesion, organ, organ capsule, adiposity, or lymph node.

The subject in need of treatment refers to a subject that has, for example, an autoimmune or inflammatory disease. Examples of autoimmune or inflammatory diseases include, but are not limited to rheumatoid arthritis, multiple sclerosis, psoriasis, inflammatory bowel disease, graft versus host disease, and sepsis.

According to one aspect of the invention, a method of isolating LSSC is provided. The method comprises digesting lymphoid tissue fragments using a combination of an enzyme mix and agitation, and then collecting the LSSC. The digestion of the lymphoid tissue fragments may be performed in a series of steps comprising:

(i) incubating the lymphoid tissue fragments with an enzyme mix;
(ii) agitating the tissue using a pipette followed by incubation to allow large fragments to settle;
(iii) removing the supernatant and repeating steps (i) and (ii) until all fragments are digested; and
wherein the LSSC are collected by pooling all supernatant fractions followed by centrifugation to obtain cell pellets.

In embodiments, the isolated LSSC are grown in a culture medium comprising a basal cell culture medium supplemented with one or more of a growth factor, serum, a platelet lysate, and an antibiotic. In embodiments, the isolated LSSC may be grown at a density of 1-10,000 cells/cm². In embodiments, the isolated LSSC are grown at 0.1-21% partial pressure of oxygen. In some embodiments, the LSSC may be grown until the LSSC are substantially free of non-LSSC. In some embodiments, the LSSC are grown until the number of stromal cells increases by at least 10%, 20%, 30%, 40%, 50%, 75%, 100%, 200%, or more. In some embodiments, the population containing LSSC is enriched for LSSC by removing hematopoietic cells or other non-stromal cells, or by growing the population of cells under conditions that favor stromal cell growth over the growth of non-stromal cells. Such conditions are described herein.

In one embodiment, the enzyme mix comprises a culture medium, Dispase, Collagenase and DNaseI. The LSSC may be derived from lymph nodes, spleen, thymus, tonsils, adenoids, and/or Peyer's patches. In some embodiments, the LSSC isolated using the methods described herein may be to use to suppress an immune response in a subject.

According to one aspect of the invention, a composition comprising isolated lymphoid tissue-derived suppressive stromal cells (LSSC) is provided. The LSSC can be isolated using the methods described above.

According to one aspect of the invention, a pharmaceutical preparation comprising a composition of isolated lymphoid tissue-derived suppressive stromal cells (LSSC) is provided. The LSSC may be isolated by treating lymphoid tissue fragments using one or more of a chemical, mechanical, and electrical cell separation process, and then by collecting the LSSC.

In some embodiments, the isolated LSSC are expanded through cell culture. In some embodiments, the isolated LSSC are ex vivo expanded cells. In some embodiments, the isolated LSSC are expanded by growing the collected cells until the LSSC are substantially free of non-LSSC.

In some embodiments, the isolated LSSC co-express CD140a and PD-L2. In some embodiments, the isolated LSSC co-express CD140a and LTBR. In some embodiments, the isolated LSSC co-express CD140a, PD-L2 and LTBR. In some embodiments, the isolated LSSC express at least one other lymphoid marker selected from the group consisting of PD-L1, Thy-1, MADCAM-1, MYH11, IL-7R, or ITGA7. In some embodiments, the isolated LSSC express at least one factor selected from the group consisting of IL-6, CCL19, CCL21, or VEGF.

The LSSC may be isolated from a species selected from the group consisting of human, non-human primate, canine, feline, equine, swine, bovine, and rodent. The LSSC can suppress T cell proliferation in vivo or in vitro.

Each of the embodiments and aspects of the invention can be practiced independently or combined. Also, the phraseology and terminology used herein is for the purpose of description and should not be regarded as limiting. The use of "including", "comprising", or "having", "containing", "involving", and variations thereof herein, is meant to encompass the items listed thereafter and equivalents thereof as well as additional items.

These and other aspects of the inventions, as well as various advantages and utilities will be apparent with reference to the Detailed Description. Each aspect of the invention can encompass various embodiments as will be understood.

All documents identified in this application are incorporated in their entirety herein by reference.

BRIEF DESCRIPTION OF THE DRAWINGS

FIG. 2A shows the viability of single cell suspensions prepared using a low-mortality enzymatic digestion method. n=6, mean+standard deviation. FIG. 2B shows the typical flow cytometric profiles of lymph node stromal subsets freshly isolated from skin-draining or mesenteric lymph nodes of individual mice. FIG. 2C shows lymph node stromal subsets identified in situ on cryosections of murine lymph node. Top panel: T cell zone FRCs (podoplanin+ CD31−) and high endothelial venules (podoplanin− CD31+ with cuboidal morphology). Two examples of HEVs are designated using arrows. Middle panel designates the medullary LECs (podoplanin+CD31+) and large medullary blood vessels (podoplanin−CD31+). Medullary lymphatic vessel/s are shown using arrows. Bottom panel: Capsular afferent LECs (Lyve1+ MadCAM+), MRCs (subcapsular, Lyve1− MadCAM+) and FDCs (follicular, Lyve1−, MadCAM+). Colocalization overlay shown in white on merged images. Original magnification: 200×. FIG. 2D shows human lymph nodes (non-mesenteric origin) digested and stained for flow cytometric analysis. Dotplots are representative of n=4 independent experiments.

FIG. 3A shows lymph node cellularity. FIG. 3B shows the proportion of CD45 negative lymph node stromal subsets. FIG. 3C shows the number of lymph node stromal subsets. FIG. 3D demonstrates MadCAM+ cells shown as a proportion of total FRCs or LECs. FIG. 3E shows the total number of MadCAM+ FRCs or LECs. FIG. 3F shows the cellularity of skin-draining lymph nodes isolated from age-matched $Rag^{-/-}$ or WT (B6) mice. FIG. 3G shows the number of lymph node stroma from age-matched $Rag^{-/-}$ or WT mice. FIG. 3G shows the number of lymph node stroma from age-matched Rag−/− or WT mice. FIG. 3H shows the proportion, or FIG. 3I the number of MadCAM+ FRCs (MRCs) or LECs in SLN of age-matched Rag−/− or WT mice. Plots are representative of n=5 mice. FIG. 3J shows the mean fluorescence intensity (MFI) of MadCAM staining in MRCs or MadCAM+ LECs. WT=wildtype. *$P<0.05$; **$P<0.01$ Mann-Whitney U Test. n=5-10 mice from 2-3 independent experiments.

In FIG. 4A skin-draining lymph nodes from 6-10 C57Bl/6 mice were enzymatically digested and enriched for CD45− stromal cells using autoMACS. The number of CD45− stroma added to the column (input) and retrieved from the column (output) were charted. Data depict n=5 independent experiments. In FIG. 4B the percent stromal cell yield for autoMACS enrichment of stroma was calculated. FIG. 4C shows the flow cytometric profiles of stromal cells pre- and post-autoMACS enrichment. FIG. 4 shows the sorting strategy and post-sort purity for major lymph node stromal cell subsets. Dotplots gated on CD45− propidium iodide− stroma.

FIG. 5A shows the microarray analysis comparing FRCs sorted from skin-draining (SLN) or mesenteric lymph nodes (MLN). Dotplot depicts P-value versus fold-change for SLN versus MLN for 15,486 selected probes. Probes upregulated in SLN are shown in red, while probes upregulated in MLN are blue; ($P<0.05$ and fold change >2; t-test). n=4-5 independent replicates. FIG. 5B shows the genes enriched in SLNs encoding cytokines and cytokine receptors (KEGG pathway mmu04060; $P<0.015$; modified Fisher's exact test with Benjamini correction). The fold-increase in mean expression in SLNs compared to MLNs is shown.

In FIG. 6A, lymph nodes were digested, and single cell suspensions put into culture for 5 days, then trypsinized and stained for flow cytometric profiling. Stromal cells were identified using CD45 (left panel), then stained with CD31 and podoplanin (right panel, gated on CD45− stroma). In particular, CD45 is a marker for hematopoietic cells, and is not present on stromal cells. In FIG. 6B cultured stromal cells stained for FDC-M1 or a relevant isotype control. FIG. 3C shows CD31 staining in cultured stromal cells harvested using a high trypsin or low trypsin protocol. Dotplots represent n=3 independent experiments. In FIG. 6D cultured stromal cells were harvested, then purified using autoMACS. FRCs, LECs, or mixed FRCs and LECs were plated in 2D (plastic tissue culture plates), or 3D (a matrigel and collagen gel) and cultured for a further 3 days prior to imaging. Original magnification 10×. Images represent n=2 independent experiments. In FIG. 6E, F-actin and DAPI were used to stain purified FRCs in 2D or 3D to highlight networks. Images represent n=3 independent experiments. (F) Purified FRCs were placed in 3D culture in a 96 well plate with or without PP2. After 24-36 hours, gel contraction was quantified. Images are representative of n=3 independent experiments. Bar graph depicts mean+standard deviation, $P<0.05$, t-test. In FIG. 6G purified FRCs were placed in 3D cultured with purified dendritic cells (DCs) or B cells, then images were sequentially acquired every 90 seconds. Upper panel shows stills from the captured images, original magnification: 20×. Lower panel shows a cartoon of the imaged stromal cell and the relevant migrating leukocyte. In FIG. 6H human lymph nodes were digested, and single cell suspensions put into culture for 7 days, then trypsinized and stained for flow cytometric profiling.

In FIG. 9A unfractionated human LSSC were cultured with freshly isolated splenocytes derived from wildtype or IFNγ−/− mice. Splenocytes were labeled with CFSE, which is diluted when a cell divides. T cells were then activated using anti-CD3 and anti-CD28 antibodies. Histograms depict T cells, identified through expression of the T cell antigen receptor. Ratios indicate the proportion of splenocytes to stroma. In FIG. 9B PDPN$^+$, PDPN$^-$, and unfractionated LSSCs were cultured with freshly isolated, purified human blood-derived T cells from an unrelated donor. T cells were labeled with CFSE, which is diluted when a cell divides. T cells were activated using PHA and IL-2. Histograms depict T cells, identified through expression of the T cell antigen receptor. Supernatant was collected and tested for the presence of nitrite, a conversion product of nitric oxide.

In FIG. 10A, two subpopulations of LSSCs were purified based on expression or lack of glycoprotein-36 (also known as PDPN). Both subpopulations were non-endothelial (CD31 negative) and non-hematopoietic (CD45 negative). In FIG. 10B, PDPN$^+$ LSSC PDPN$^-$ LSSC, or unfractionated LSSC were cultured with freshly isolated, purified human blood-derived T cells from an unrelated donor at a 1:5 ratio (LSSCs to T cells). T cells were labeled with CFSE, which is diluted when a cell divides. T cells were activated using PHA and IL-2. Histograms depict T cells, identified through expression of the T cell antigen receptor. Ratios indicate the proportion of splenocytes to stroma.

FIG. 16 shows that murine FRCs protect against sepsis in 2 difference mouse models when administered at therapeutic timepoints.

MSCs are a suppressive stromal cell type, but several authors have shown that their effect in sepsis, when administered as an allogeneic therapy and at a therapeutic timepoint (>60 mins after the septic insult), to be minimal or absent (Nemeth et al. 2010; Mei et al. 2010). Our results similarly showed no overall survival benefit of MSC administration, whereas allogeneic FRCs imparted a significant survival benefit.

DETAILED DESCRIPTION OF THE INVENTION

Figure 1:
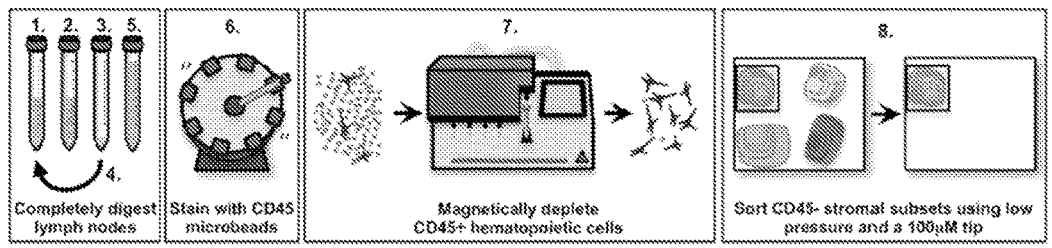
FIG. 1 shows a schematic diagram of pooled murine lymph node stromal cell digestion and preparation for cell sorting. 1. Add enzyme mix (RPMI-1640 with 0.8 mg/ml Dispase, 0.2 mg/ml Collagenase P, 0.1 mg/ml DNase I) to tissue, incubate in 37 C waterbath. 2. After 10-20 mins (see methods), agitate lymph node fragments using 1 ml pipette, then incubate until the fragments settle. 3. Remove the supernatant containing released cells, centrifuge it and store it on ice. 4. Repeat steps 1-3 until all fragments are fully digested (no more than 60 mins). 5. Pool all supernatant fractions, centrifuge, filter, and count. 6. Add anti-CD45 microbeads, incubate at 4 C on rotating wheel. 7. Use MACS or AutoMACS to deplete CD45+ cells, count. 8. Stain enriched CD45− stroma with antibodies; sort to high purity using 100 um tip at 20 psi.

The present invention, in one aspect, relates to isolated lymphoid tissue-derived suppressive stromal cells (LSSC). Described herein are methods for isolating, and expanding LSSC ex vivo in a commercially applicable manner, novel compositions comprising LSSC, and uses of LSSC, particularly therapeutic applications to suppress autologous, allogeneic and xenogeneic immune responses.

The inventors discovered that stromal cells from lymph nodes can suppress the activity of the immune system. Moreover, lymphoid tissue-derived stromal cells attract immune cells, which is not a known feature of other immunosuppressive stromal cell populations. The ability of lymphoid tissue-derived stromal cells to attract immune cells, such as T cells, B cells, NK cells, combined with their immunosuppressive function make them a surprisingly effective therapeutic tool for suppressing an immune response in a subject. The LSSC can be used to suppress the activities of T cells, B cells, NK cells, NKT cells, dendritic cells and macrophages, either alone or in concert with other immunosuppressive drugs.

Lymph nodes are important secondary lymphoid organs located at lymphatic intersections in the body, allowing efficient interaction between antigen-presenting cells and naïve T and B cells and promoting effective initiation of immune responses (Warnock et al., 1998, Mebius, 2003, Katakai et al., 2004a, Katakai et al., 2004b, Sixt et al., 2005, Bajenoff et al., 2006, Junt et al., 2008). Lymph node stromal cells also play a crucial and arguably underappreciated role in promoting the maintenance of naïve T cells (Link et al., 2007).

Lymph nodes can be dissociated and the resulting cells grown in culture. "Lymphoid tissue-derived suppressive stromal cells" refers to all cell types present in a lymphoid tissue that adhere to the tissue culture dishes and can be maintained for some length of time. The cultured cells can be a heterogeneous population and can be made up of most cells residing within lymph nodes such as fibroblastic reticular cells (FRC), follicular dendritic cells (FDCs), lymphatic endothelial cells (LEC), blood endothelial cells (BEC), and marginal reticular cells (MRC). The cultured cells also can be a homogeneous population or any selected combination of FRC, FDC, LEC, BEC and/or MRC. In some embodiments, the LSSC are isolated and expanded ex vivo using the methods described herein. The LSSC may be derived from cutaneous or mesenteric lymph nodes, spleen, thymus, tonsils, adenoids, and/or Peyer's patches. The LSSC are free of or depleted of hematopoietic LSSC. In some embodiments, the LSSC are derived from a species selected from the group consisting of human, non-human primate, canine, feline, equine, swine, bovine, and rodent.

Distinct stromal subtype cells impose the structure of the lymph node and maintain each microniche. T cell zone fibroblastic reticular cells (FRCs) express chemokines CCL19 and CCL21 to attract T cells and dendritic cells (DCs), and lay down an intricate meshwork of collagens and extracellular matrix on which these cells crawl (Ansel et al., 2000, Luther et al., 2000, Katakai et al., 2004b, Bajenoff et al., 2006, Link et al., 2007, Woolf et al., 2007). Analogous to FRCs but specialized for B cell attraction, follicular dendritic cells (FDCs) are a rare stromal subset specialized for B cell attraction and antigen presentation. FDCs are only found within B cell follicles, which they create through CXCL13 secretion (Cyster et al., 2000). The lymph node capsule is essentially an enlarged lymphatic vessel constructed from lymphatic endothelial cells (LECs), which carry interstitial fluid to the node and empty it into the parenchyma. It filters through the paracortex and cortex, eventually reaching efferent lymphatics in the medulla, which convey lymph further upstream (Mebius, 2003, Willard-Mack, 2006). Blood endothelial cells (BECs) construct cortical blood vessels and capillaries, including high endothelial venules specialized to attract naïve T cells from the bloodstream (Mebius, 2003, Willard-Mack, 2006).

Several other stromal subsets have been reported in the literature but are poorly studied, with their lineages and major functions undefined (reviewed by (Fletcher et al., 2011). Marginal reticular cells (MRCs) are a subset of CXCL13-producing stroma growing at the cortical face of the subcapsular sinus (Katakai et al., 2008). Their origin is unknown though the cells show similarities to FRCs, including podoplanin expression (Katakai et al., 2008). In the spleen, an analogous stromal subset is important for migration of immature B cells into follicles (Ansel et al., 2000). It is hypothesized that MRCs represent the postnatal equivalent of the lymphoid tissue organizer (LTo) subset (Katakai et al., 2008) which is responsible for lymph node organogenesis (Coles et al., 2010). Indeed, it has been convincingly shown that postnatal podoplanin+ splenic stroma are capable of regenerating through interaction with hematopoietic lymphoid tissue inducer cells (Scandella et al., 2008).

The LSSC are used according to the present invention to suppress an immune response. Accordingly, aspects of the present invention involves methods for suppressing an immune response by administering to a subject in need of such treatment isolated lymphoid tissue-derived suppressive stromal cells (LSSC) in an amount effective to suppress the immune response in the subject.

As used herein, "isolated" refers to the separation of a population of stromal cells away from other populations of non-stromal cells. Isolation can be effected by any procedure which separates cells, such as growing conditions, purification techniques such as the use of magnetic beads, cell sorting, or other similar techniques. In some embodiments, the LSSC are isolated using the methods described herein.

As used herein "suppressing" means reducing in degree, or severity, or extent, or duration the overt manifestations of the immune response including, for example, reduced activation of T cells or B cells, and reduced humoral and cell-mediated responses. "Suppression" can be measured, for example, by examining the presence or rate of T or B cell division in the presence or absence of LSSC, examining the release of cytokines by immune cells in the presence or absence of LSSC, measuring antibody production in the presence or absence of LSSC, or measuring CTL function in the presence or absence of LSSC Likewise, suppression of an immune response can be measured symptomatically, such as, by determining a reduction in inflammation or other symptoms associated with the disease being treated. "Suppression" of an immune response does not require complete negation or prevention of any of these manifestations of an immune response, but rather a reduction in degree or severity, or extent or duration, which is of clinical or other practical significance. In one embodiment, suppression is measured by examining the rate of cell division of pre-activated allogeneic T cells in the presence or absence of LSSC. In one embodiment, suppression is measured by examining the rate of lethality in mice with graft-versus-host disease in the presence or absence of LSSC. In one embodiment, suppression is measured by examining the rate of lethality of acute septic shock in mice.

In some embodiments, a subject in need of such treatment has an autoimmune or inflammatory disease.

The term 'autoimmune or inflammatory disease' refers to those disease states and conditions wherein the immune response of the patient is directed against the patient's own constituents resulting in an undesirable and often terribly debilitating condition. As used herein, 'autoimmune or inflammatory disease' is intended to further include autoimmune conditions, syndromes and the like. Example of autoimmune or inflammatory diseases include, but are not limited to, rheumatoid arthritis, multiple sclerosis, psoriasis, inflammatory bowel disease, graft-versus-host disease and sepsis.

In some embodiments, a subject in need of treatment is a subject identified as having one or more of conditions described above, i.e. the subject has been diagnosed by a physician (e.g., using methods well known in the art) as having a disease or condition described above. In some embodiments, the subject in need of treatment is a subject suspected of having or developing a disease or condition described above, such as a subject presenting one or more symptoms indicative of a disease or condition described above (e.g. extreme fatigue or joint pain). In some embodiments, a subject in need of treatment is a subject with one or more risk factors for developing an autoimmune or inflammatory disease. Risk factors include but are not limited to gender, age, genetic predisposition, previous incidents of autoimmune or chronic inflammatory disease, and lifestyle. The term "subject in need of treatment" further includes people who once had a disease or condition described above but whose symptoms have ameliorated.

In some embodiments, a subject in need of treatment has or is suspected of having an autoimmune or inflammatory disease. The subject may display, for example, abnormal titres of autoantibodies.

The subject is an animal, typically a mammal. In one aspect, the subject is a dog, a cat, a horse, a sheep, a goat, a cow or a rodent. In important embodiments, the subject is a human.

The LSSC are administered in an effective amount. An effective amount is a dose sufficient to provide a medically desirable result and can be determined by one of skill in the art using routine methods. In some embodiments, an effective amount is an amount which results in any improvement in the condition being treated. In some embodiments, an effective amount may depend on the type and extent of the disease or condition being treated and/or use of one or more additional therapeutic agents. However, one of skill in the art can determine appropriate doses and ranges of therapeutic agents to use, for example based on in vitro and/or in vivo testing and/or other knowledge of compound dosages.

When administered to a subject, effective amounts of the therapeutic agent will depend, of course, on the particular disease being treated; the severity of the disease; individual patient parameters including age, physical condition, size and weight, concurrent treatment, frequency of treatment, and the mode of administration. These factors are well known to those of ordinary skill in the art and can be addressed with no more than routine experimentation. In some embodiments, a maximum dose is used, that is, the highest safe dose according to sound medical judgment.

In the treatment of an autoimmune or inflammatory disease, an effective amount is that amount which slows the progression of the disease, halts the progression of the disease, or reverses the progression of the disease. An effective amount includes that amount necessary to slow, reduce, inhibit, ameliorate or reverse one or more symptoms associated with the autoimmune or inflammatory disease. In some embodiments, such terms refer to a reduction in the swelling of one or more joints or a reduction in the pain, fatigue and/or fever associated with the autoimmune or inflammatory disease. In some embodiments, such terms refer to a reduction in the levels of circulating autoantibodies associated with the autoimmune or inflammatory disease. In some embodiments, such terms refer to a reduction in a human's PASI score. In some embodiments, such terms refer to an improvement in a human's global assessment score.

In some embodiments, at least 0.1 million LSSC are administered to the subject on a per kilogram subject basis in one or more dose administrations, for one or several days (depending of course of the mode of administration and the factors discussed above). In some embodiments, at least 1 million LSSC are administered to the subject on a per kilogram subject basis. In some embodiments, at least 10 million LSSC are administered to the subject on a per kilogram subject basis. Actual dosage levels of the therapeutic agent can be varied to obtain an amount that is effective to achieve the desired therapeutic response for a particular patient, compositions, and mode of administration. The selected dosage level depends upon the activity of the particular compound, the route of administration, the tissue being treated, and prior medical history of the patient being treated. However, it is within the skill of the art to start doses of the compound at levels lower than required to achieve the desired therapeutic effort and to gradually increase the dosage until the desired effect is achieved.

In some embodiments, the LSSC that are administered to the subject are ex vivo expanded cells. The LSSC are expanded ex vivo by growing the cells in a culture medium. The isolated LSSC may be grown in a culture medium, for example, comprising a basal cell culture medium supplemented with one or more of a growth factor, serum, a platelet lysate, and an antibiotic. In some embodiments, the isolated LSSC are grown, for example, in a minimum essential medium (MEM) alpha medium supplemented with fetal calf serum and penicillin/streptomycin. In some embodiments, the LSSC that are administered to the subject are substantially free of non-LSSC. In some embodiments, the LSSC are autologous, allogeneic or xenogeneic with respect to the subject.

Pharmaceutical preparations comprising the LSSC are administered to a subject by any suitable route. For example, compositions can be administered to the subject by intravenous, intraperitoneal, intra-arterial, subcutaneous, or intramuscular injection or by local administration on or into a lesion, organ, organ capsule, adiposity, or lymph node.

In some embodiments, the LSSC are on or in a two or three dimensional framework which is implanted into the subject. Implants or matrices include polymeric matrices such as fibrous or hydrogel based devices. The implant may be biodegradable or non-biodegradable. Fibrous or hydrogel implants can be manufactured or constructed using commercially available materials. The implants are typically formed of a natural or a synthetic polymer. The LSSC are seeded onto the implant by application of a cell suspension to the implant. This can be accomplished by soaking the implant in a cell culture container or injection or other direct application of the cells to the implant. The implant seeded with cells is implanted using standard surgical techniques. The implant can be seeded and cultured in vitro prior to implantation, seeded and immediately implanted or implanted and then seeded with cells. In the preferred embodiment cells are seeded onto and into the implant and cultured in vitro for between approximately ten hours and two weeks.

Some aspects of the invention involve a method of isolating lymphoid tissue-derived suppressive stromal cells (LSSC). The method comprises digesting lymphoid tissue fragments using a combination of an enzyme mix and agitation and then collecting the LSSC. In some embodiments, the digestion of the lymphoid tissue fragments is performed in a series of steps comprising: (i) incubating the lymphoid tissue fragments with an enzyme mix; (ii) agitating the tissue using a pipette followed by incubation to allow large fragments to settle; (iii) removing the supernatant and repeating steps (i) and (ii) until all fragments are digested. The LSSC are then collected by pooling all supernatant fractions followed by centrifugation to obtain cell pellets. In some embodiments, the enzyme mix comprises a culture medium, Dispase, Collagenase and DNase I. The LSSC may be derived from cutaneous or mesenteric lymph nodes, spleen, thymus, tonsils, adenoids, and/or Peyer's patches. The isolated cells may be used to suppress an immune response as described above.

The isolated LSSC can be grown in a culture medium comprising a basal cell culture medium supplemented with one or more of a growth factor, serum, a platelet lysate, and an antibiotic. In some embodiments, the LSSC are grown in a minimum essential medium (MEM) alpha medium supplemented with fetal calf serum and penicillin/streptomycin. In some embodiments, the isolated LSSC are grown at 0.1-21% partial pressure of oxygen. In some embodiments, the isolated LSSC are grown at 2.5-21% partial pressure of oxygen.

In some embodiments, the LSSC are grown until the LSSC are substantially free of non-LSSC. In some embodiments, the LSSC are grown until the number of stromal cells increases by at least 10%, 20%, 30%, 40%, 50%, 75%, 100%, 200%, or more. In some embodiments, the isolated LSSC are grown at a density of 1-10,000 cells/cm$^2$. In some embodiments, the isolated LSSC are grown at a density of 10-500 cells/cm$^2$.

According to some aspects of the invention, a composition is provided. The composition comprises isolated lymphoid tissue-derived suppressive stromal cells (LSSC), wherein the LSSC are isolated by the methods described herein. For example, the LSSC are isolated by digesting lymphoid tissue fragments using a combination of an enzyme mix and agitation and then collecting the LSSC.

According to some aspects of the invention, a pharmaceutical preparation is provided. The pharmaceutical preparation comprises a composition of isolated lymphoid tissue-derived suppressive stromal cells (LSSC). The LSSC may be isolated by treating lymphoid tissue fragments using one or more of a chemical, mechanical, and electrical cell separation process, and then by collecting the LSSC. For example, the cells may be separated by enzymatic or chemical digestion, physical disruption and agitation, and/or by using electric fields.

The isolated LSSC may be expanded through cell culture. In some embodiments, the isolated LSSC are ex vivo expanded cells. In some embodiments, the isolated LSSC are expanded by growing the collected cells until the LSSC are substantially free of non-LSSC. The cells may be grown in a culture medium comprising a basal cell culture medium supplemented with one or more of a growth factor, serum, a platelet lysate, and an antibiotic.

In some embodiments, the isolated LSSC co-express platelet derived growth factor receptor, alpha polypeptide (PDGFRα or CD140a) and programmed cell death ligand 2 (PD-L2 or CD273). In some embodiments, the isolated LSSC co-express CD140a and lymphotoxin β receptor (LTBR). In some embodiments, the isolated LSSC co-express CD140a, PD-L2 and LTBR. The isolated LSSC may also express one or more other lymphoid marker selected from the group consisting of programmed cell death 1 ligand 1 (PD-L1), Thy-1 cell surface antigen (Thy-1), mucosal vascular addressin cell adhesion molecule 1 (MADCAM-1), myosin heavy chain 11 (MYH11), interleukin 7 receptor (IL-7R), or integrin alpha 7 (ITGA7). In some embodiments, the isolated LSSC express at least one factor selected from the group consisting of interleukin 6 (IL-6), chemokine (C—C motif) ligand 19 (CCL19), chemokine (C—C motif) ligand 21 (CCL21), or vascular endothelial growth factor (VEGF).

The LSSC may be isolated from a species selected from the group consisting of human, non-human primate, canine, feline, equine, swine, bovine, and rodent, and suppress T cell proliferation in vitro.

The pharmaceutical preparations of the present invention may include or be diluted into a pharmaceutically-acceptable carrier. The term "pharmaceutically-acceptable carrier" as used herein means one or more compatible fillers, diluants or other such substances, which are suitable for administration to a human or other mammal such as a dog, cat, or horse. The term "carrier" denotes an organic or inorganic ingredient, natural or synthetic, with which the active ingredient is combined to facilitate the application. The carriers are capable of being commingled with the preparations of the present invention, and with each other, in a manner such that there is no interaction which would substantially impair the desired pharmaceutical efficacy or stability. Carriers suitable for oral, subcutaneous, intravenous, intramuscular, etc. formulations can be found in Remington's Pharmaceutical Sciences, Mack Publishing Company, Easton, Pa.

The present invention is further illustrated by the following Example, which in no way should be construed as further limiting. The entire contents of all of the references (including literature references, issued patents, published patent applications, and co-pending patent applications) cited throughout this application are hereby expressly incorporated by reference.

EXAMPLES

Materials and Methods
Mice

Male C57Bl/6 mice aged 4-6 wk were obtained from the Jackson Laboratory. Mice used for ImmGen sorting were precisely age-matched to 6 weeks. Male C57BL/6 Rag$^{-/-}$ mice were obtained from Taconic. All mice were rested for 5 days post-transport, and were specific pathogen free and cared for in accordance with institutional and National Institutes of Health guidelines. Experimental procedures were conducted with the approval of the Research Animal Care subcommittee at the Dana-Farber Cancer Institute.
Human Lymph Nodes Human lymph nodes were procured from cadaveric donors through the National Disease Research Interchange (NDRI) resource center (Philadelphia, USA). Intact lymph nodes were transported in DMEM on ice, and processed for flow cytometry or cell culture within 24 hours.
Antibodies For flow cytometry, cell sorting and cryosection staining of mouse lymph node stroma, the following antibodies were used: anti-CD45 (clone 40-F11, BD Biosciences), anti-podoplanin (clone 8.1.1, Developmental Studies Hybridoma Bank), anti-CD31 (clone MEC13.3, Biolegend), anti-Lyve 1 (clone 10.1.1, a kind gift from Dr. Andrew Farr), and anti-MadCAM (clone MECA-367, eBioscience). Propidium iodide and clone TER119 (Biolegend) were used where appropriate to exclude dead cells and erythrocytes. For staining human cells, antibodies used were: anti-CD45 (clone HI30, Biolegend), anti-CD31 (clone WM59, BD Biosciences) and anti-podoplanin (clone NZ-1, AngioBio Co), detected with highly cross-adsorbed anti-rat IgG (H+L) Alexa-488 (Invitrogen).

Enzymatic Digestion of Lymph Nodes from Individual Mice

For flow cytometric analysis or cell culture, lymph nodes from individual mice were dissected, pierced once with fine forceps, and placed in 5 ml of RPMI-1640 on ice. Where use of skin-draining lymph nodes was specified, we dissected axillary, brachial and inguinal lymph nodes. After all lymph nodes were dissected, RPMI-1640 was removed and replaced with 2 ml of freshly-made enzyme mix comprised of RPMI-1640 containing 0.8 mg/ml Dispase and 0.2 mg/ml Collagenase P (both from Roche), and 0.1 mg/ml DNase I (Invitrogen). Tubes were incubated at 37 C in a waterbath and gently inverted at 5 min intervals to ensure the contents were well-mixed. After 20 mins, lymph nodes were very gently aspirated and expirated using a 1 ml pipette, which disrupted the capsule and released most leukocytes. The mixture was replaced in the waterbath and large fragments were allowed to settle for 30 seconds, after which the enzyme mix was removed and added to 10 ml of ice-cold FACS buffer (2% FCS, 5 mM EDTA in PBS) and centrifuged (300 g, 4 min, 4 C). 2 ml of fresh enzyme mix was added to the digestion tube, the contents gently mixed using a 1 ml pipette, and incubated, with regular gentle mixing using a 1 ml pipette. After 10 min, the cells were mixed vigorously for 30 seconds using a 1 ml pipette. Fragments were again allowed to settle, the supernatant was removed and added to the previously spun cell pellet, and 2 ml of fresh enzyme mix was added to the digestion tube. From here, the digestion mix was vigorously mixed using a 1 ml pipette every 5 mins until, when held up to light, it was clear that all remaining lymph node fragments were completely digested. This procedure, from the time of first incubation to complete digestion, usually took 50 mins, and never longer than 60 mins. Supernatants were centrifuged after each removal (300 g, 4 min, 4 C) until finally, each collection tube contained the entire cellular contents of an individual mouse's harvested lymph nodes. Cells were filtered through 80 μm nylon mesh, counted using a hemocytometer, and assessed for viability using trypan blue. Viability exceeded 95%. 5×106 cells per stain were then incubated with 50 μl diluted antibodies for 20 min at 4 C in ice-cold FACS buffer (2% FCS, 5 mM EDTA in PBS) before acquisition on a FACSCalibur or FACSAria IIu (BD Biosciences).
Enzymatic Digestion and Stromal Enrichment of Lymph Nodes from Pooled Mice for Cell Sorting and Large-Scale Isolation Digestion of multiple pooled mice generally proceeded as described in 2.1, with changes as follows (depicted graphically in FIG. 1): lymph nodes from 4-10 mice were pooled in a single tube and digested using 5 ml of enzyme mix per digestion step. After lymph nodes were fully digested, and the cells centrifuged and counted, the single cell preparation was enriched for non-hematopoietic stromal cells using CD45 microbeads and the autoMACS system (both from Miltenyi). We used 7 μL beads per 107 cells, incubated in FACS buffer for 20 min on a rotating wheel at 4 C. The labeled fraction was then depleted using the Depletes program, according to the manufacturer's instructions. Enriched stroma were then counted and stained using a high volume of antibody (100 μL of diluted antibody cocktail per $10^6$ cells) for cell sorting.
Enzymatic Digestion of Human Lymph Nodes Human lymph nodes were carefully cleaned of fat and connective tissue, then cut into small pieces (<0.5 cm) using fine scissors. Digestion proceeded according to section 2.4, however enzyme concentration was increased to 2.4 mg/ml Dispase and 0.6 mg/ml Collagenase P (both from Roche), and 0.3 mg/ml DNase I (Invitrogen) in RPMI-1640. In some cases we did not digest the entire organ, and instead took a random selection of approx. 20 mixed fragments, representing all areas of the node. After 60 mins, lymph node fragments were completely digested, and were then filtered, counted and where required stained, as detailed above.

Low Pressure Flow Cytometric Stromal Cell Sorting

Flow cytometric sorting of stromal cells is improved when a specialized low-pressure, large aperture setup is used; however there are technical challenges inherent in resetting a sorter to a non-standard specification and then successfully sorting pure populations. We used FACSAria or upgraded FACSAria IIu machines utilizing FACSDiva software (all from BD Bioscience) set to 20 psi and fitted with a 100 µm tip. While each machine will differ, we have found that the following approximate specifications have applied to at least 4 different FACSAria machines set up for stromal sorting. These differ from the suggested setups specified by the manufacturer.

Decreased stream pressure increases droplet size, such that only 5-6 droplets are visible through the stream visualization window at 20 psi, instead of 10-12 droplets at 70 psi. While the droplet breakoff point directly affects sort success and should always be visible, it is possible for the satellite resolution point to occur below view while sorting at low pressure, even after increasing the droplet frequency. This does not preclude a successful sort; however, it is important to be confident that satellite resolution occurs no more than 1-2 droplets below the screen. This can be reasonably established in 2 ways: first, by temporarily adjusting the droplet breakoff point higher and out of view, so that the satellite resolution point becomes visible, and counting the number of droplets between breakoff and resolution before readjusting downwards; and second, by looking at the decreasing distance between satellite and droplet, and estimating the number of droplets until resolution occurs. The satellites, if not resolved on-screen, should be very close to resolution.

Critically, deciding whether to apply the attenuation control (which dampens droplet amplitude) alters subsequent specifications considerably. Sample setup sort reports both with and without attenuation are provided for reference (Table 1). BD Biosciences manual recommends attenuation not be applied when sorting at 20 psi; however, we found it necessary at times with the FACSAria (but not FACSAria IIu) to generate a good stream. While a manual adjustment of the 100 m tip was required to generate a good stream using the FACSAria, we have not had to move the tip or utilize attenuation for the FACSAria IIu system, where the o-ring is permanently fitted.

Lastly, we have noted that the 633 nm laser delay can suddenly change when low pressure is engaged. The reasons for this are unclear, but we recommend using CST beads to set delays, or testing laser function using SPHERO Rainbow particles (BD Bioscience) (or any similar calibration check). Note that a lack of signal from the 633 nm laser may require re-calibration of the laser delay.

Compensation for a stromal cell sort should be strictly performed using enriched stromal cells. Stroma are large cells with a degree of accompanying autofluorescence. A machine compensated using leukocytes yields suboptimal resolution of populations when stroma are sorted. Enriched stroma should be used to compensate, because in unenriched populations, stroma are usually rare, and we find that the autocompensation software cannot differentiate between normal levels of autofluorescence in a digested single cell suspension and true stromal staining.

When the machines are optimally calibrated, sorting proceeds with excellent resolution of sorting streams and good efficiency. Sort streams should resolve well as bright, discrete dots in the sort window; 'spraying' of the sorting streams should not be evident.

AutoMACS-enriched stroma were routinely sorted to high purity (>95%) into TRIzol (Invitrogen). After gating on $CD45^-$ propidium iodide$^-$ stroma, subsets were sorted as follows: fibroblastic reticular cells (FRCs), podoplanin$^+$ $CD31^-$; lymphatic endothelial cells (LECs), podoplanin$^+$ $CD31^-$; blood endothelial cells (BECs), podoplanin$^-CD31^+$; double negative stromal cells (DNs), podoplanin$^-CD31^-$.

Microarray Assays and Analysis

RNA from 10,000-15,000 sorted cells was isolated as previously described (Yamagata et al., 2004), then amplified and hybridized to Affymetrix GeneChip Mouse Gene 1.0 ST Arrays (Santa Clara, Calif., USA) using the GeneChip Whole Transcript Sense Target Labeling Assay according to the manufacturer's instructions. This yielded whole-transcript information using probes designed to bind in multiple locations across each gene. Raw data was normalized using the robust multi-array average (RMA) preprocessing algorithm (performing background adjustment, quantile normalization and summarization) (Irizarry et al., 2003), in the Expression File Creator module of GenePattern. Probe lists were analyzed for expression in at least one subset (excluded if mean expression value <120 across all subsets), and for low variance among replicates (excluded if coefficient of variation >0.5 in either population). We used the Multiplot module of GenePattern to calculate differences between skin lymph node FRCs and mesenteric lymph node FRCs. Differences were considered for further analysis if the fold change in expression was >2 and P<0.05 (student's T test). Output data lists were ranked using Microsoft Excel, and gene lists were analyzed for enrichment across KEGG pathways using the DAVID program's Functional Annotation tool (NIAID, david.abcc.ncifcrf.gov (Dennis et al., 2003)), and with Affymetrix exon background set to the MoGene-1_0-st-v-1 chip. KEGG pathway analyses with T-test P-values <0.05 after multiple hypothesis (Benjamini) correction were considered significant. The NCBI GEO accession number for the data series is GSE15907.

Lymph Node Stromal Cell Culture Techniques

Lymph nodes were digested as detailed above, then counted, and plated at a concentration of 5×105 cells/cm2. Cell culture media was αMEM supplemented with 10% batch-tested, low Ig FCS, and 1% Penicillin/Streptomycin. Plates were washed after 24 hours to remove non-adherent cells. After 5 days, mouse cell cultures primarily contained LECs and FRCs. Human cell cultures grew more slowly and were harvested after 7 days. Human lymph node stromal cell cultures primarily contained FRCs and DNs. A non-standard harvesting protocol was routinely utilized, consisting of a short incubation in low-concentration Trypsin with EDTA to minimize trypsin-based shearing of important cell surface markers (Table 2). Cells were washed with PBS to remove residual protein, and harvest buffer (0.2% Trypsin with 5 mM EDTA in PBS) was added to culture plates. Cells were incubated in harvest buffer at 37 C for 2 mins. At this point, their morphology became rounder, and an equal volume of complete media was immediately added to wells. Cells were washed from the plate with gentle agitation using a 1 ml pipette, and supernatant was added to another equal volume of complete media for centrifuging (300 g, 3 minutes, 4 C). FRCs and LECs were replated, sorted, or MACS-purified from this preparation as required.

For three-dimensional cultures and network analyses, cells were cultured in deformable matrices constructed from 3.2 mg/ml of high concentration rat tail Collagen I (BD Biosciences), 1.8 mg/ml Matrigel basement membrane matrix (BD Bioscience), 8.3% (v/v) of 5× αMEM stock made in-house from αMEM powder (Invitrogen), and 30% (v/v) culture media containing cells to be plated. Gel components were mixed on ice and 200 µl plated onto plastic, or glass-bottomed culture dishes for imaging (MatTek). Gels were left to set at 37 C for 10 mins before being covered with culture media. For contraction assays, gels were created in flat-bottomed 96 well culture plates and photographed after 15 hours. Contraction was measured using the following equation: area contracted gel ($cm^2$)/area well ($cm^2$)*100=% contraction. For time-lapse live cell imaging, bone-marrow derived dendritic cells or B cells were mixed at a 5:1 ratio with purified cultured FRCs. During imaging, gels were incubated at 37 C with 10% CO2 in αMEM containing 10% FCS. Movies depict time-lapse imaging with 1 frame acquired every 90 seconds.

Immunohistology and Confocal Microscopy

Lymph nodes were freshly dissected and fixed in 10% paraformaldehyde for 4 hours, then left in 10% sucrose solution overnight. Blocks were then embedded in OCT compound (VWR) and snap-frozen, then stored at −80° C. Lymph nodes were cryosectioned (7 µm) using a Leica cryostat, and acetone fixed, then blocked for 30 min using 2% BSA. After washing in PBS, sections were stained with primary antibody for 60 mins, then washed and stained with secondary antibody for a further 60 mins. Slides were mounted with a coverslip using fluorescent mounting medium (DAKO) and stored at 4 C. Images were acquired using a Leica Sp5 confocal microscope.

Statistical Analysis

GenePattern's Multiplot program was used to calculate T-test P values on normalized, array data where the coefficient of variance between replicates for any sample was <0.5. A P-value of <0.05 was considered significant if the fold-change observed was also <2. Genes were tested for KEGG pathway association using the DAVID program (david.abcc.ncifcrf.gov), which compared data using a modified Fisher's Exact Test, and a T-test with a Benjamini multiple hypothesis correction, to show enrichment of 2 or more genes in a particular list. The non-parametric Mann-Whitney U test was used to compare flow cytometric data (Prism).

Lymph Node Stromal Cell Isolation and Culture

C57Bl6/J mice aged 3-6 weeks were used as FRC donors. Cutaneous and mesenteric lymph nodes were dissected and digested using enzymatic and mechanical means. Lymph nodes from 10 mice were incubated in: 0.8 mg/ml Dispase, 0.2 mg/ml Collagenase P, and 0.1 mg/ml DNase in RPMI-1640, for 60 minutes at 37 C, with regular agitation and replacement of the enzyme mixture. Digested cells were recovered via centrifugation. Once digestion was complete, cells were resuspended in RPMI-1640, filtered through 80 µm mesh, and counted using a hemocytometer and trypan blue. Cells were plated into culture flasks at 5×$10^5$ cells/$cm^2$. Culture media consisted of 10% batch-tested low Ig FCS with 1% penicillin/streptomycin in αMEM. Cells were washed after 24 hours, grown for a further 6 days, then passaged once using 0.2% Trypsin and 5 mM EDTA in PBS and split at a 1:10 ratio for expansion for a further 5-6 days before use.

MSC Isolation and Culture

MSCs were harvested from the bone marrow of FRC donor mice described above. Femurs and tibias were removed from 10 mice. The marrow was recovered by centrifugation and resuspended in sterile RPMI-1640 using a pipette. Cells were plated into culture flasks at 5×$10^5$ cells/$cm^2$. Culture media consisted of 10% batch-tested low Ig FCS with 1% penicillin/streptomycin in αMEM. Cells were washed after 24 hours, grown for a further 6 days, then passaged once using 0.2% Trypsin and 5 mM EDTA in PBS and split at a 1:10 ratio for expansion for a further 5-6 days before use.

FRC and MSC Purification

Cells were harvested using 0.2% Trypsin and 5 mM EDTA in PBS, then counted using a hemocytometer and trypan blue (viability exceeded 95%), and resuspended in 1 ml FACS buffer (PBS with 2% FCS and 5 mM EDTA), with 10 ul anti-CD31-biotin and 10 ul anti-CD45-biotin, per $10^7$ cells. After 15 mins cells were washed and incubated with anti-biotin microbeads and passed through a MACS LS column according to the manufacturer's instructions (Miltenyi Biotec). MACS-purified FRCs were used for all studies.

Sepsis Induction: LPS Model

C57Bl6/J mice aged either 3-6 weeks (young) or 18-24 months (aged) received a single injection of LPS, resulting in sterile sepsis. Young mice received 300 µg LPS i.p. in 100 ul saline, and aged mice received 150 µg i.p. in 100 ul saline. 1×$10^6$ FRCs were administered as a single injection i.p. at the stated timepoint, in saline. Mice were euthanized if they reached any of the following endpoints: loss of consciousness, inability to be roused, inability to stand, or a sustained drop in breathing rate below 20 breaths/10 seconds.

Sepsis Induction: CLP Model

Balb/c mice received cecal ligation and puncture (CLP), resulting in polymicrobial sepsis. Briefly, mice were anesthetized and a midline incision made through skin and peritoneal muscle. The cecum was located and externalized onto a sterile surgical field, then 80% of the cecum was ligated using 6.0 suture, and the cecum punctured twice using a 23 g needle. A small droplet of fecal matter was exuded before the cecum was replaced and the muscle and skin closed. Mice received 1 ml saline s.c. At the stated timepoint, mice received a single i.p. injection of either saline or 1×$10^6$ allogeneic FRCs in saline. At this time, antibiotic treatment also commenced for all mice (15 mg ampicillin in saline injected i.p.). Antibiotics were administered every 12 hours. Mice were euthanized if they reached any of the following endpoints: loss of consciousness, inability to be roused, inability to stand, or a sustained drop in breathing rate below 20 breaths/10 seconds.

Cytokine Array

Blood was obtained as detailed above, and plasma collected by centrifugation. Concentration of analytes was obtained using the Luminex MAGPIX assay and reader with xPONENT software, according to manufacturer's instructions.

Induction of Colitis Model

Female C/B17.scid mice aged 8 weeks were used as colitis recipients. Female Balb/c donors aged 7 weeks were used as cell donors to induce colitis. Spleens, and cutaneous and mesenteric lymph nodes were dissected from 20 Balb/c mice and suspended using mechanical disruption into RPMI-1640. Cells were filtered and counted, then enriched for naïve CD4+ T cells using a $CD4^+CD62L^+CD44^{low}$ isolation kit (R&D Systems), according to the manufacturer's instructions. $CD4^+CD45RB^{hi+}$ T cells were then sorted using FACS, and resuspended in sterile RPMI-1640. 15 C/B17.scid mice received 5×$10^5$ cells i.v. in 100 ul RPMI-1640. Mice began to lose weight 2 weeks post-colitis induction, indicating disease onset. Mice then received $1 \times 10^6$ allogeneic FRCs injected i.p. twice per week for the duration of the study. Mice were euthanized if they reached any of the following endpoints: loss of >20% of their starting bodyweight, or hindlimb paralysis.

Results

Enzymatic Isolation of Mouse and Human Lymph Node Stromal Cells

The study of lymph node stromal cells has gathered recent momentum, with several high-impact papers dissecting their newly discovered roles in maintaining (Link et al., 2007) and deleting (Lee et al., 2007, Nichols et al., 2007, Gardner et al., 2008, Magnusson et al., 2008, Yip et al., 2009, Cohen et al., 2010, Fletcher et al., 2010) naïve T cells. Methodological capabilities, however, have been a limiting factor.

We therefore aimed to develop a low-mortality enzymatic digestion protocol which would enable highly reproducible isolation of lymph node stromal cells with low variability. Using a combination of enzymatic and physical dissociation (FIG. 1), we routinely isolated stromal cells with >95% viability (FIG. 2A) using trypan blue on whole lymph node suspensions (1.5% stroma) immediately after isolation. Six hours after isolation and stromal enrichment, the average viability of stroma using propidium iodide was 87.8%±0.8 (mean±standard deviation, n=3 experiments). This high viability also allowed us to characterize and compare the number of each stromal subset present in individual mice, and was a key factor in successfully sorting and culturing these cells. We used CD45, podoplanin, CD31 and MadCAM (FIG. 2B) to study 5 major subsets of lymph node stroma. The MadCAM+ MRC subset, in particular, has not previously been isolated for flow cytometric analysis.

Figure 2:
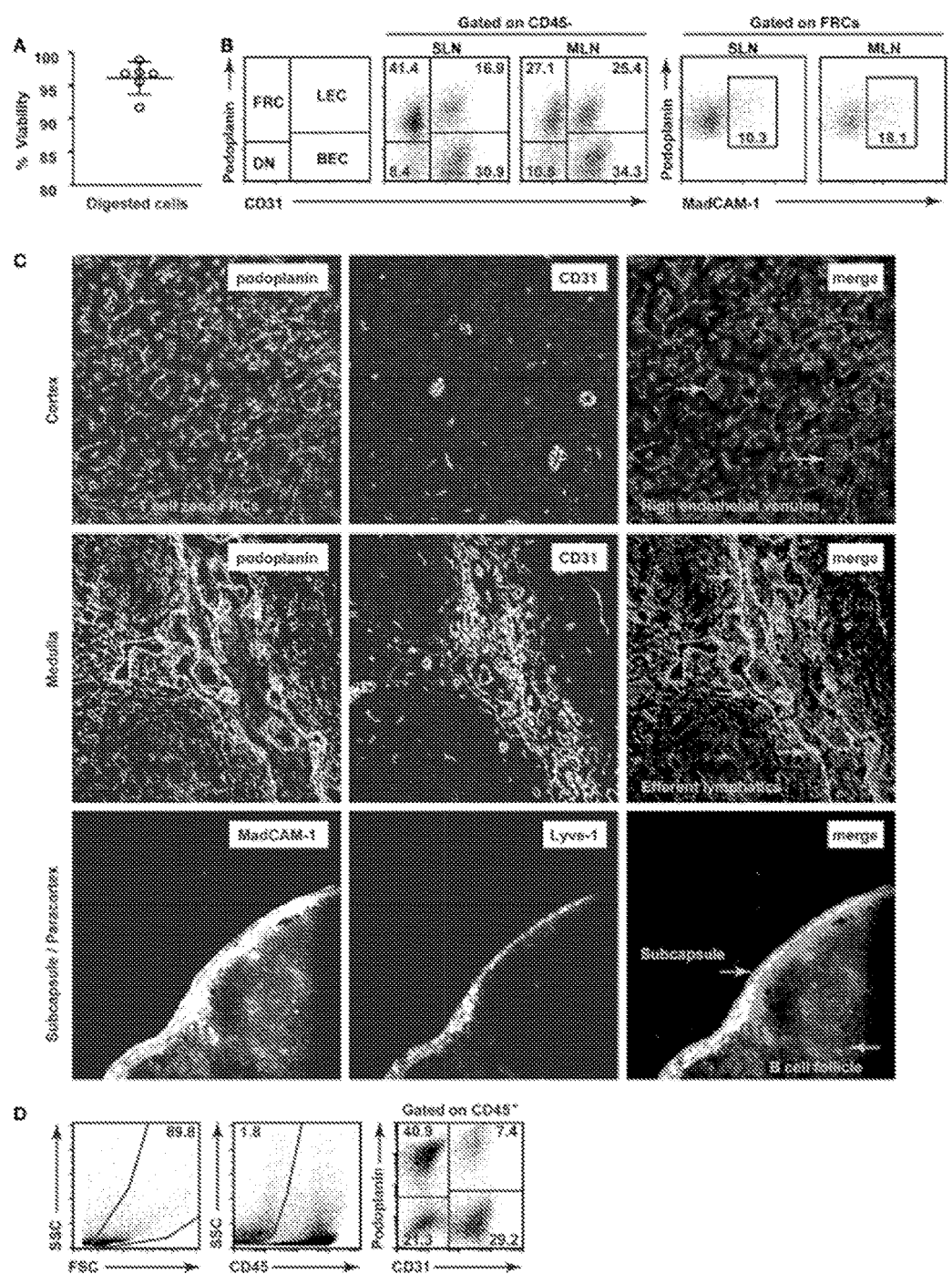
FIG. 2 shows the validation of a low-mortality method for isolation of lymph node stromal subsets.

We first directly compared our flow cytometric strategies to previously defined in situ histological analyses of stromal subsets (FIG. 2C). Our aim was to establish methods that would enable changes in stromal architecture to be monitored in parallel with changes to number or proportion of cell types, mRNA profile, and other techniques requiring cell isolation.

Accordingly, we found that FRCs, as defined by flow cytometry, created a reticular network throughout the T cell zone as expected (top panel). BECs expressed CD31 but not podoplanin and were primarily present in the cortex (top panel), with high endothelial venules distinguishable by their small size and cuboidal morphology. LECs, defined by coexpression of podoplanin and CD31, lined large lymphatic vessels in the hilar region of the medulla (middle panel) and subcapsule (data not shown). This hilar region also contained large blood vessels (CD31$^+$ podoplanin$^-$. MadCAM$^+$ reticular cells lined the subcapsule (bottom panel) and MadCAM staining was also present in the B cell zone, as previously reported. We found that subcapsular LECs (shown here expressing Lyve-1) also expressed MadCAM (bottom panel), making the subcapsule a MadCAM-rich region of the lymph node. Phenotypically, MRCs formed a subset within the podoplanin$^+$ CD31$^-$ FRC gate by flow cytometry (FIG. 2B).

We hypothesized that our isolation methods could be applied to isolate human lymph node stroma, allowing the creation of useful ex-vivo experimental systems. Human lymph node stromal architecture is well described by histology (Link et al., 2011) but subsets have not been isolated for flow cytometry or other immunological studies.

We acquired human lymph nodes of non-mesenteric origin from cadaveric donors. While increased enzyme concentration was required to digest the lymph nodes (see Methods), once digested, their stromal composition was markedly similar to mice (compare FIGS. 2D and 2B). These results suggest that murine lymph node stromal cell techniques may be equally applicable to human studies.

Mesenteric Lymph Nodes Contain Fewer FRCs than Skin-Draining Lymph Nodes

To further validate our digestion, we tested its reproducibility by assessing how much the proportional makeup of lymph node stromal cell subsets varied between age-matched mice. We also compared the stromal composition of skin-draining and mesenteric lymph nodes. While these lymph nodes have well-established structural similarities and are well-studied by histology, their ontogenies occur at different times and are dependent on different signaling pathways (Mebius, 2003). Additionally, mesenteric lymph nodes are continually exposed to gut and gastromucosally-derived antigens, while skin-draining lymph nodes are not.

Figure 3:
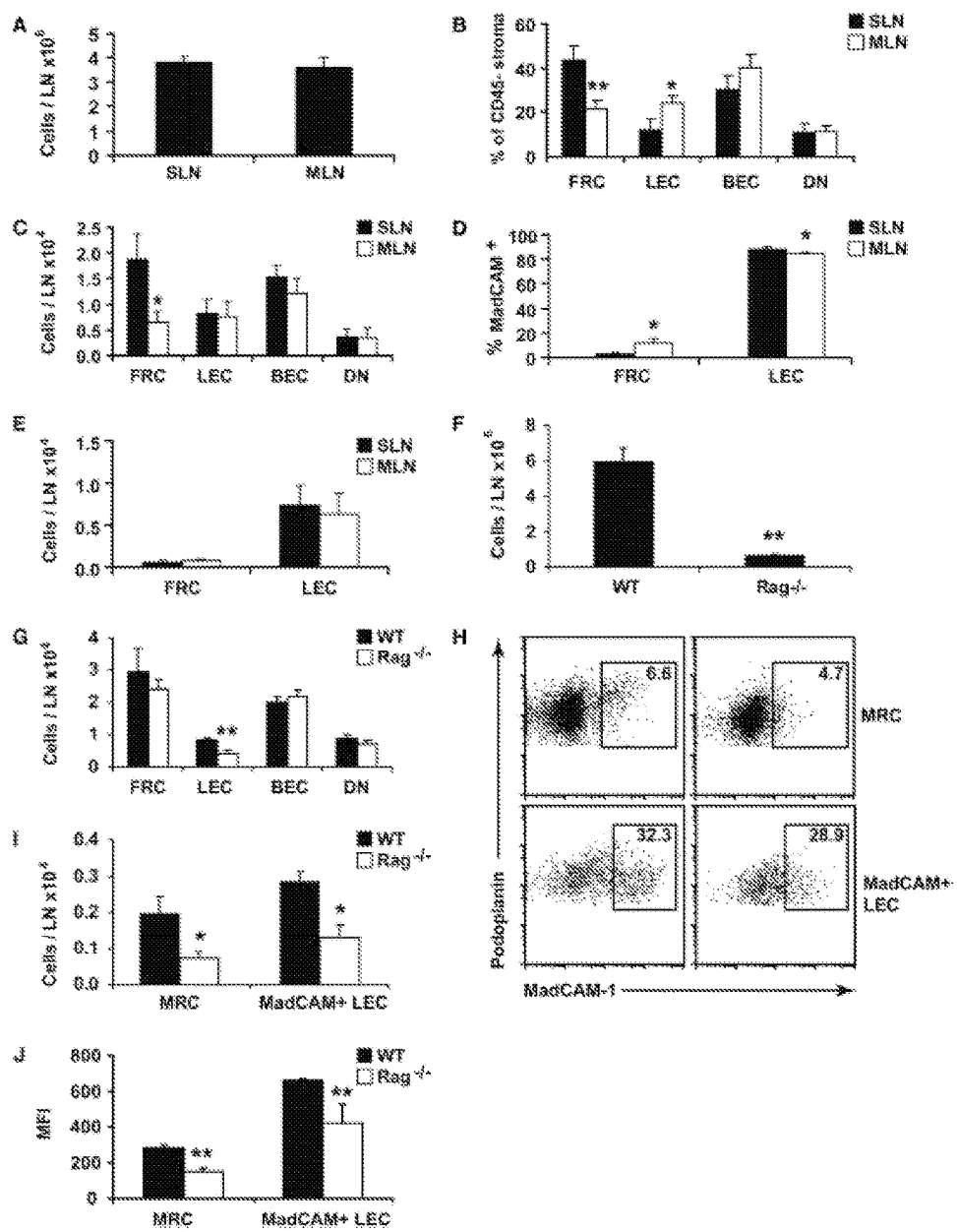
FIG. 3 demonstrates that lymph nodes show site-specific alterations in stromal composition. Lymph nodes from individual C57Bl/6 mice were digested and stained for flow cytometry.

Surprisingly, we found that while similar numbers of cells were isolated from each skin-draining or mesenteric lymph node (FIG. 3A), the stromal composition significantly differed (FIG. 3B). FRCs, which grow throughout the T cell zone, were present at greater frequency (FIG. 3B, FIG. 2B), and were more numerous (FIG. 3C) in skin-draining lymph nodes than mesenteric lymph nodes. LECs, BECs, DNs and MRCs were present at similar numbers in both sites (FIG. 3C), making the difference FRC-specific.

We asked whether this difference was due to skewing in the proportions of the MRC subset (Katakai et al. 2008) which, we found, falls within the FRC gate (FIG. 2B). 10-20% of cells within the FRC gate expressed MadCAM in 5 week old male mice, with a higher proportion in mesenteric lymph nodes than skin-draining lymph nodes (FIG. 2B, 3D). However, while MRC proportions were significantly altered between sites, similar to LECs, their overall numbers were not (FIG. 3E). This suggests that MRC numbers and FRC numbers are differently regulated, since MRCs, like the other stromal subsets, are numerically similar between sites, while FRCs are reduced in mesenteric lymph nodes.

In some lymphoid organs, such as the thymus, the numbers of predominant stromal cell subsets expand or shrink in parallel with developing T cells. We tested whether this applied to the FRC population using Rag$^{-/-}$ mice, which lack T and B cells. FRCs develop in Rag$^{-/-}$ lymph nodes, but it is not known whether they expand and contract in response to lymphocyte numbers. This question is particularly relevant to infection, since lymph nodes must expand dramatically in a short time to contain proliferating lymphocytes.

While Rag$^{-/-}$ mice had smaller lymph nodes (FIG. 3F), they possessed normal numbers of FRCs compared to age-matched wildtype controls (FIG. 3G). The number of LECs, however, was significantly reduced, suggesting that their numerical homeostasis is linked to the presence of mature lymphocytes. Rag$^{-/-}$ FRCs did not differ from WT in rates of cell turnover (data not shown), and after injecting LPS into mice, the number of FRCs did not expand alongside T and B cells (data not shown). FRC numbers were therefore maintained completely independent of mature lymphocytes under lymphopenic, steady-state, and inflammatory conditions.

Surprisingly, we found that the MRC subset was under-developed in Rag$^{-/-}$ mice (FIG. 3H-J). It is reported that MadCAM+ MRCs exist by histology in Rag$^{-/-}$ mice (Katakai et al., 2008), but in our hands, both the numbers of MadCAM+ MRCs and the amount of MadCAM protein per MRC were significantly reduced (FIG. 2H-J). This also applied to MadCAM$^+$ LECs (FIG. 3H-J), suggesting that upregulation of MadCAM expression in both cell types denotes a developmental stage requiring the presence of lymphocytes, though expression of the protein itself can occur in their absence. While the proportion of MadCAM+ LECs was similar between WT and Rag$^{-/-}$ (FIG. 3H), the significant reduction in total LECs (FIG. 3G) translated to reduced numbers of MadCAM+ LECs (FIG. 3I).

Enriching and Sorting Lymph Node Stromal Cell Subsets

Figure 4:
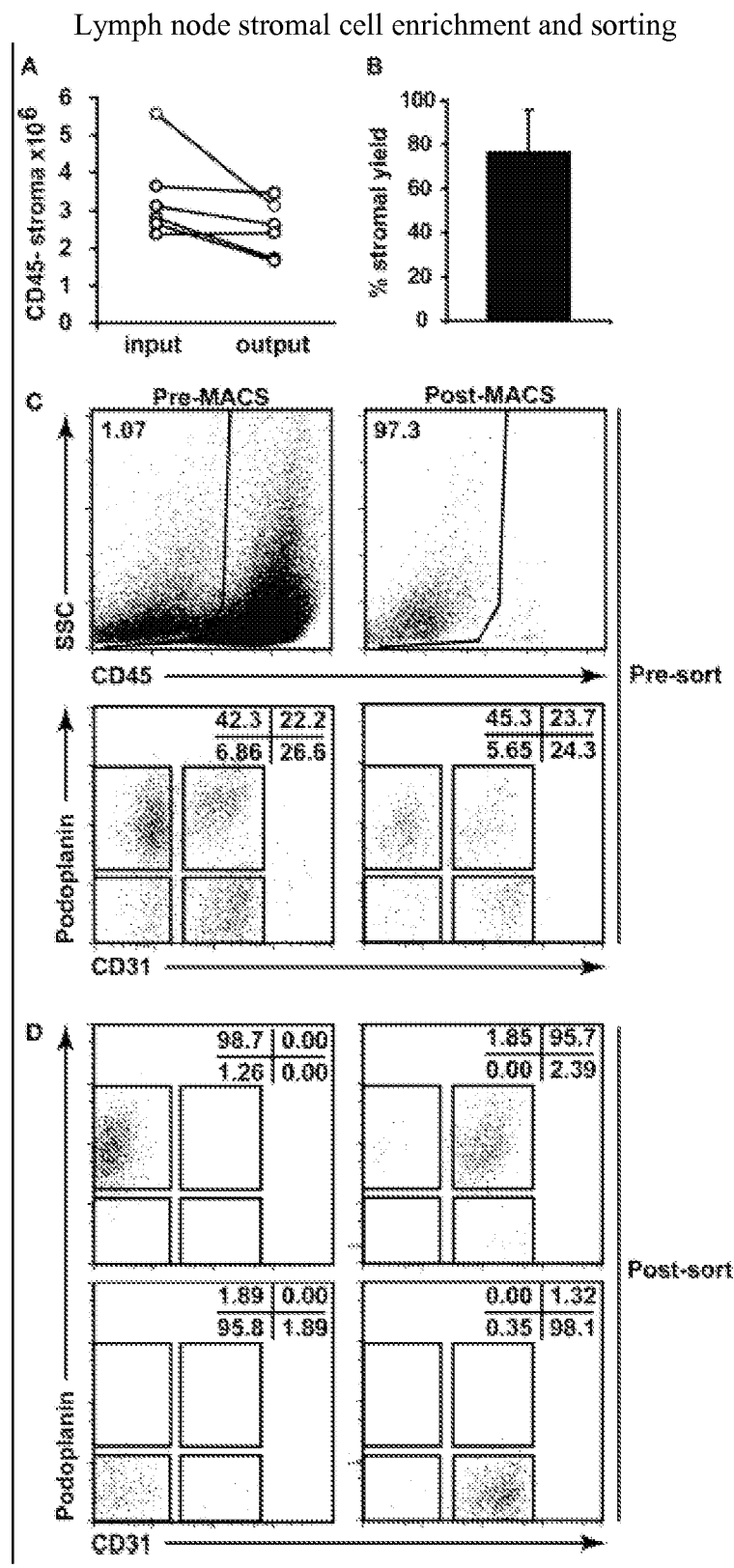
FIG. 4 shows the lymph node stromal cell enrichment and sorting.

Following the successful digestion of lymph nodes, we next adapted the means to successfully sort and culture the stromal cells. Sorting stromal cells can be technically difficult (see methods) and we used MACS-based depletion of hematopoietic cells to decrease sorting times and increase the resulting purity. This additional step yielded minimal loss of stroma (FIG. 4A, B) and did not appreciably alter the stromal composition; we saw no selective loss of stromal subsets post-MACS (FIG. 4C) and, after sorting, achieved excellent purity (FIG. 4D).

Using this method, we sorted FRCs from skin-draining and mesenteric lymph nodes as part of the multicenter ImmGen Consortium. This involved transcriptomic analysis of cells sorted under highly controlled, minimally variable conditions, with the overall aim of generating a public database to provide a comprehensive, cross-referenced map of the immunological genome.

FRCs from skin-draining and mesenteric lymph nodes were analyzed for expression of 25,194 probes to yield a list of 11,162 probes expressed above an arbitrary threshold (mean expression value >120) in either skin-draining or mesenteric lymph nodes. These probes were also filtered for a low (<0.5) coefficient of variance between replicates.

Figure 5:
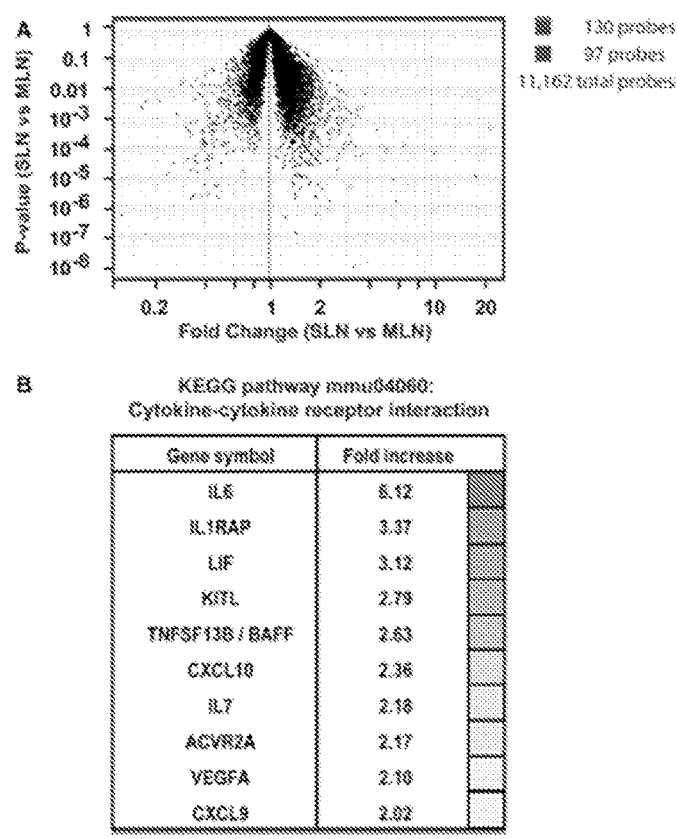
FIG. 5 shows site-specific transcriptional upregulation of cytokines in murine FRCs from skin-draining lymph nodes.

We first confirmed that FRCs from these different locations shared expression of previously published FRC-specific markers such as CD140a, CCL19, and IL-7 (data not shown), then analyzed the data for differences. Comparing skin-draining vs mesenteric lymph node FRCs, a volcano plot depicting fold-change and P-value showed that 130 probes were significantly upregulated in FRCs from skin-draining compared to mesenteric lymph nodes, while expression of 97 probes was significantly higher in mesenteric lymph node FRCs compared to skin-draining (>2 fold change, P<0.05) (FIG. 5A). After mapping the probes to unique genes, these data corresponded to upregulation of 126 genes in skin-draining lymph node FRCs (data not shown) and 54 genes in mesenteric lymph node FRCs (data not shown)

We were interested in whether these lists contained evidence for activation of particular gene pathways, or gene networks uniquely operating in either cell type, as a clue to any site-specific specialization. Using the free online program DAVID (version 6.7; National Institute of Allergy and Infectious Diseases), we used a network analysis tool (KEGG) to comb the lists for known biological connections between these genes, then used statistical analysis tools to assess whether the connected genes appeared together at a frequency greater than would be expected by chance. The KEGG pathway mmu04060, which covers cytokine-cytokine receptor interaction, was significantly enriched in FRCs from skin-draining lymph nodes compared to mesenteric (genes appeared at a frequency 4.8-fold higher than expected by chance, Benjamini corrected P value=0.0055). This list included ten genes of immunological relevance (FIG. 5B) upregulated in skin-draining lymph node FRCs by at least twofold. Genes upregulated in mesenteric lymph nodes were not significantly enriched in an identifiable KEGG pathway, but notably included genes involved in regulating the growth of fibroblasts, genes relevant to the gut microenvironment, such as those involved in retinoic acid metabolism or MadCAM expression, endothelial cell crosstalk, extracellular matrix secretion, and outgrowth of peripheral neurons (Table 3).

Cultured FRCs Mimic In Vivo Function and Support Leukocyte Migration

Figure 6:
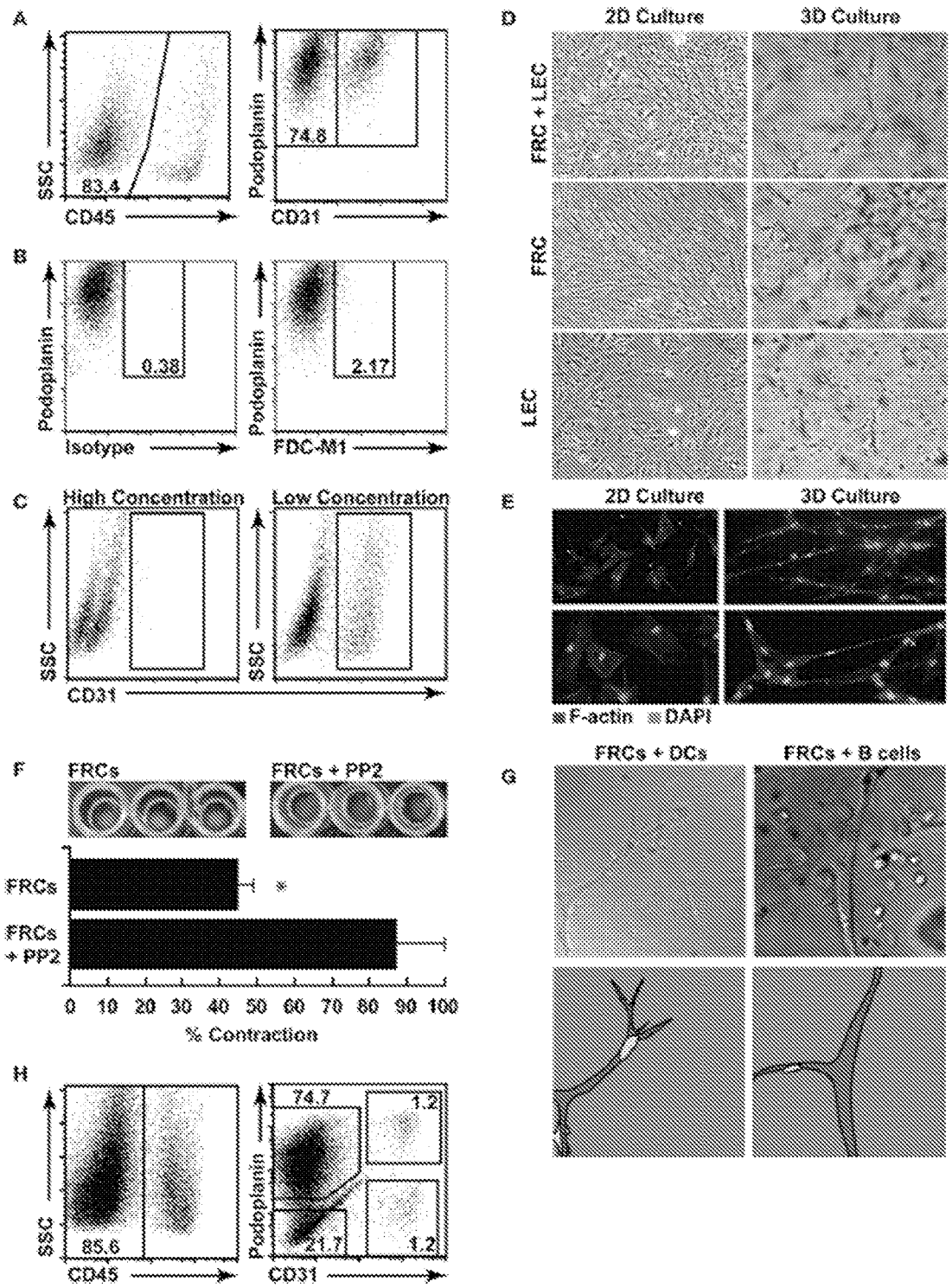
FIG. 6 shows the three-dimensional (3D) culture of murine FRCs mimics in vivo function.

We next tested the ability of lymph node stroma to grow in culture. We found that stroma from a successfully digested lymph node cell suspension will readily adhere to tissue culture plates within 2 hours of plating and begin to expand at the expense of CD45+ leukocytes, which form less than 10% of the culture after 5 days (FIG. 6A). FRCs and LECs readily grew in culture, while BECs and DN cells did not (FIG. 6A). FDCs did not grow in culture (FIG. 6B). Importantly, our low-trypsin, high EDTA harvesting protocol allowed retention of important surface markers such as CD31 (FIG. 6C) and CD140a (not shown; see table 2). We found that $5 \times 10^5$ cells/cm2, containing approx. $5 \times 10^3$ stromal cells, routinely yielded approx. $1.5-2 \times 10^4$ stroma/cm2 after 5 days of culture. This culture system enabled easy expansion and manipulation of FRCs, LECs and MRCs.

FRCs in particular became highly polarized in two-dimensional (2D) culture (FIG. 6D) showing strong F-actin stress fibers (FIG. 6E). This did not mimic their morphology in vivo; so, using an optimized mix of Collagen I, matrigel, and enriched αMEM, we also explored three-dimensional (3D) culture of FRCs and LECs, as a tool to examine their function when permitted to expand and connect in three dimensions as they do in vivo. We found that FRCs stretched and formed extensive networks when grown in 3D (FIG. 6D, E), while LECs preferred a flat surface and grew more successfully in 2D culture (FIG. 6D). Interestingly, neither cell type grew to overconfluence under 3D conditions (data not shown), suggesting an innate regulation of cell density that did not occur in 2D culture. To validate the biological relevance of this in vitro FRC network, we performed two experiments. First, we placed a high number of FRCs into a small matrigel plug, and monitored their ability to contract the gel (FIG. 6F). FRCs express high levels of alpha smooth muscle actin and are highly contractile (Link et al., 2007). We found that FRCs contracted the gel with high efficiency, and that this contraction was prevented when the Src tyrosine kinase inhibitor PP2 was added to the gel. Second, we added bone marrow derived dendritic cells (DCs) or spleen-derived lymphocytes to a gel containing FRCs, and used a live-imaging approach to find that, as reported in vivo, DCs and lymphocytes crawled efficiently and preferentially along the FRC network (stills are shown in FIG. 6G with full time-lapse movies shown in Supplementary Movies 1 and 2).

Using the same methods, we successfully cultured human lymph node stromal cell subsets. Unlike murine cells, BECs and DN cells grew in vitro alongside LECs and FRCs (FIG. 6H).

Together, these results showed that murine lymph node stroma were readily isolated for flow cytometry and sorting, and could be cultured in the absence of leukocytes, yet created extensive 3D networks on which leukocytes would readily crawl, as reported in vivo. Our data suggested that human lymph node stroma were similarly amenable to study using murine techniques.

Together, these results describe the validation of a suite of techniques applicable to the study of lymph node stromal cells in mice and humans, under a variety of ex vivo and in vitro conditions.

Figure 7:
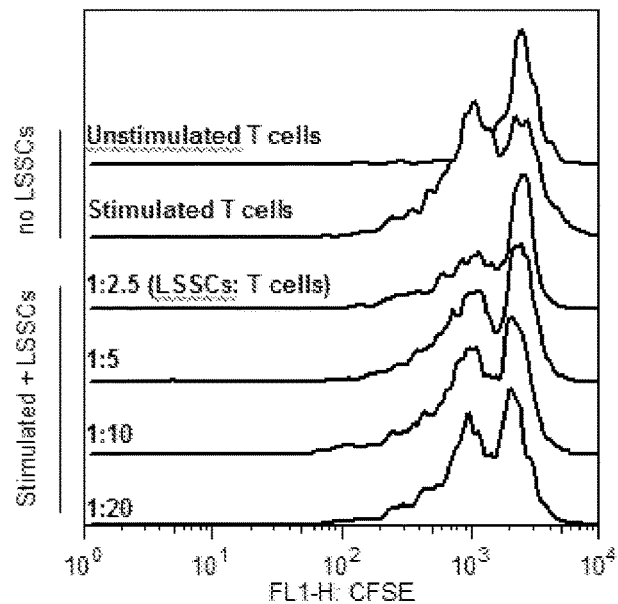
FIG. 7 shows that human lymphoid tissue-derived suppressor cells suppress the proliferation of activated allogeneic splenocytes. Unfractionated LSSCs were cultured with freshly isolated human splenocytes from an unrelated donor. Splenocytes were labeled with CFSE, a fluorescent dye that is diluted when a cell divides. T cells within the splenocyte population were activated using PHA and IL-2. Histograms depict T cells, identified through expression of the T cell antigen receptor. Ratios indicate the proportion of splenocytes to stroma.

Lymphoid Tissue-Derived Suppressor Cells Suppress the Proliferation of Activated Allogeneic Splenocytes Unfractionated LSSCs were cultured with freshly isolated human splenocytes from an unrelated donor. Splenocytes were labeled with CFSE, a fluorescent dye that is diluted when a cell divides. T cells within the splenocyte population were activated using PHA and IL-2. FIG. 7 shows histograms depicting T cells, identified through expression of the T cell antigen receptor. Ratios indicate the proportion of splenocytes to stroma. T cells stimulated without cultured stromal cells dilute their CFSE more than cells cultured with LSSCs, and LSSCs suppress T proliferation in a dose-dependent manner (FIG. 7).

LSSCs Suppress the Proliferation of Activated, Xenogeneic T Cells

Figure 8:
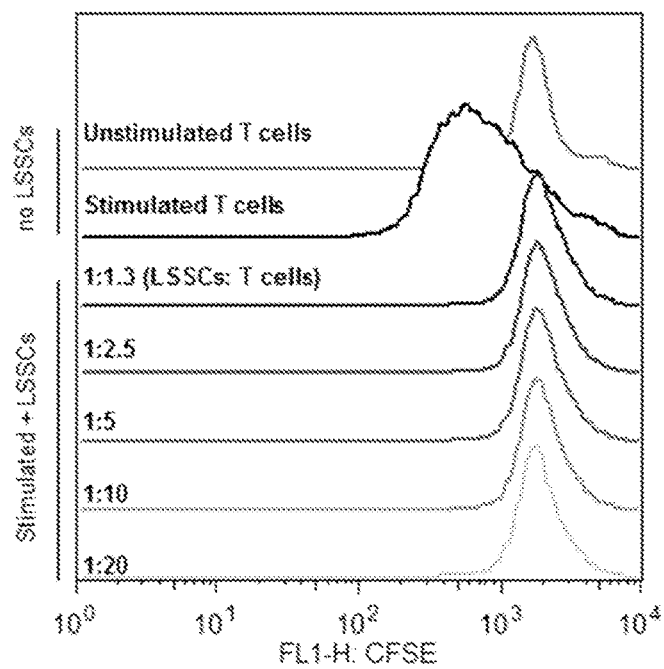
FIG. 8 shows that human LSSCs suppress the proliferation of activated, xenogeneic T cells. Unfractionated LSSC were cultured with freshly isolated mouse splenocytes. Splenocytes were labeled with CFSE, which is diluted when a cell divides. T cells were then activated using anti-CD3 and anti-CD28 antibodies. Histograms depict T cells, identified through expression of the T cell antigen receptor. Ratios indicate the proportion of splenocytes to stroma.

Unfractionated LSSC were cultured with freshly isolated mouse splenocytes. Splenocytes were labeled with CFSE, which is diluted when a cell divides. T cells were then activated using anti-CD3 and anti-CD28 antibodies. FIG. 8 shows histograms depicting T cells, identified through expression of the T cell antigen receptor. Ratios indicate the proportion of splenocytes to stroma. Blood-derived T cells stimulated without cultured stromal cells dilute their CFSE more than cells cultured with LSSCs, Both PDPN+ and PDPN− LSSC subpopulations are equally capable of suppressing T cells. LSSCs are potent suppressors of xenogeneic responses (compare with allogeneic suppression shown in FIG. 7).

LSSCs Suppress T Cell Proliferation Via Novel Mechanisms

In mice, a PDPN+ stromal cell derived from lymph nodes suppresses autologous T cell proliferation via mechanisms critically requiring T cell-derived IFNg, and stromal cell-derived nitric oxide (Lukacs-Kornek et al. Nature Immunology, 2011). We wanted to test whether our LSSCs suppressed T cell responses using these same mechanisms.

Figure 9:
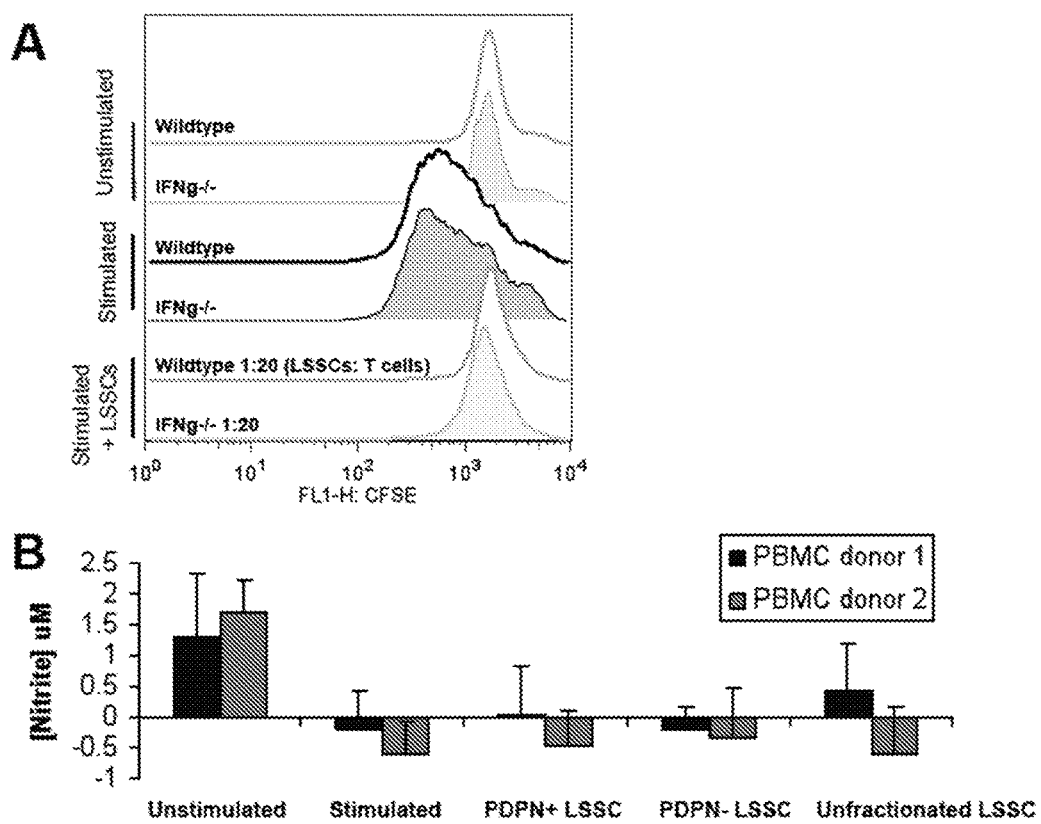
FIG. 9 shows that LSSCs suppress T cell proliferation via novel mechanisms.

Unfractionated LSSC were cultured with freshly isolated splenocytes derived from wildtype or IFNg−/− mice. Splenocytes were labeled with CFSE, which is diluted when a cell divides. T cells were then activated using anti-CD3 and anti-CD28 antibodies. FIG. 9A shows histograms depicting T cells, identified through expression of the T cell antigen receptor. Ratios indicate the proportion of splenocytes to stroma.

PDPN+, PDPN−, and unfractionated LSSCs were cultured with freshly isolated, purified human blood-derived T cells from an unrelated donor. T cells were labeled with CFSE, which is diluted when a cell divides. T cells were activated using PHA and IL-2. FIG. 9B shows histograms depicting T cells, identified through expression of the T cell antigen receptor. Supernatant was collected and tested for the presence of nitrite, a conversion product of nitric oxide.

It was found that LSSCs suppressed IFNg−/− T cells equally well as wildtype T cells. Neither PDPN+ nor PDPN− LSSC subpopulations, nor unfractionated LSSCs produced detectable nitric oxide/nitrite in the suppression assay. LSSCs suppress T cell proliferation using novel, IFNg and nitric oxide-independent mechanisms and are therefore significantly different from the mouse PDPN+ lymph node stromal population.

Figure 10:
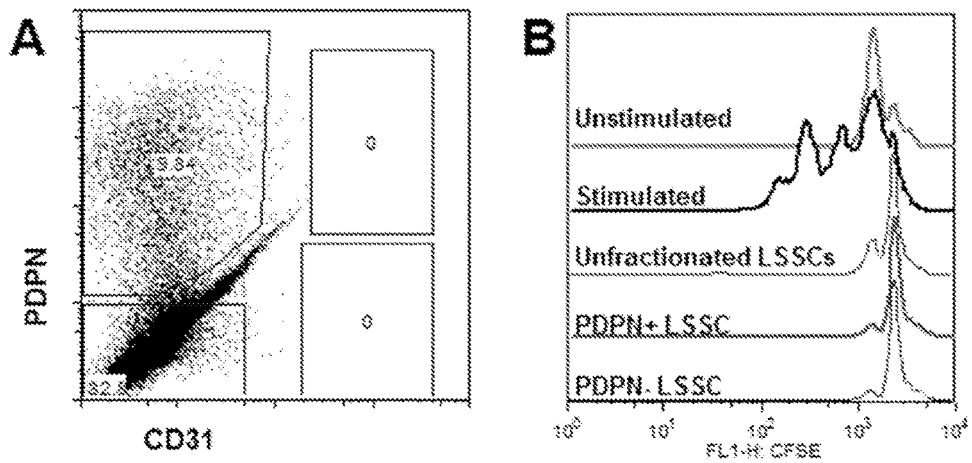
FIG. 10 shows that two major subpopulations of human lymphoid tissue-derived suppressor cells each suppress the proliferation of activated allogeneic T cells.

Two Major Subpopulations of Lymphoid Tissue-Derived Suppressor Cells Each Suppress the Proliferation of Activated Allogeneic T Cells In FIG. 10A, two subpopulations of LSSCs were purified based on expression or lack of glycoprotein-36 (also known as PDPN). Both subpopulations were non-endothelial (CD31 negative) and non-hematopoietic (CD45 negative). PDPN+ LSSC, PDPN− LSSC, or unfractionated LSSC were cultured with freshly isolated, purified human blood-derived T cells from an unrelated donor at a 1:5 ratio (LSSCs to T cells). T cells were labeled with CFSE, which is diluted when a cell divides. T cells were activated using PHA and IL-2. FIG. 10B shows histograms depicting T cells, identified through expression of the T cell antigen receptor. Ratios indicate the proportion of splenocytes to stroma.

It was observed that blood-derived T cells stimulated without cultured stromal cells dilute their CFSE more than cells cultured with LSSCs, Both PDPN+ and PDPN− LSSC subpopulations are equally capable of suppressing T cells.

LSSCs Halt the Division of Pre-Activated Allogeneic T Cells

Some therapeutic applications for LSSCs would require their transfusion or transplantation into individuals with an ongoing immune response. We therefore wanted to see whether LSSCs could suppress pre-activated T cells.

Figure 11:
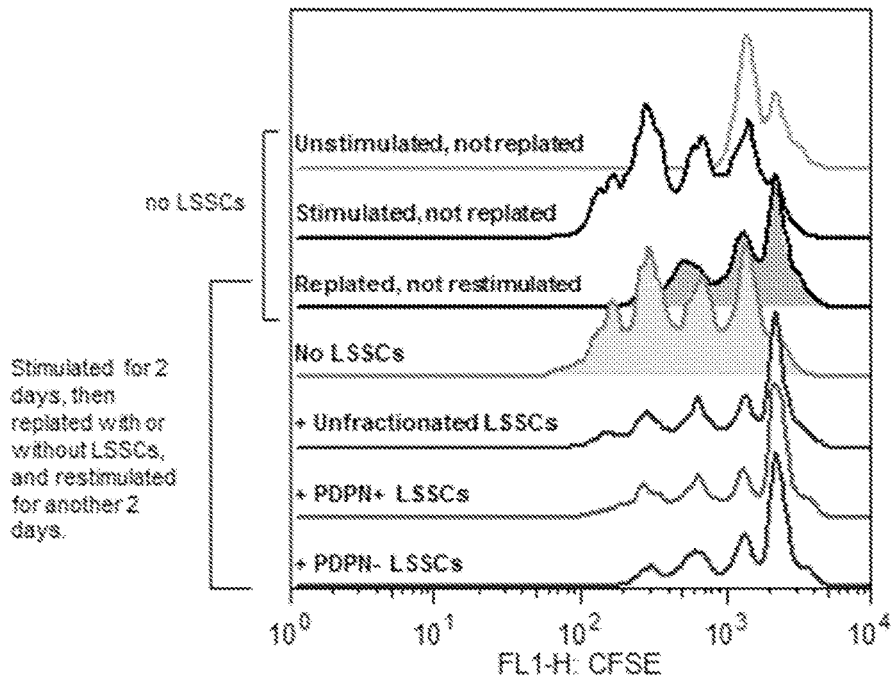
FIG. 11 shows that human LSSCs halt the division of pre-activated allogeneic T cells. PDPN+ LSSC, PDPN− LSSC, or unfractionated LSSC were cultured with freshly isolated, purified human blood-derived T cells from an unrelated donor. T cells were labeled with CFSE, which is diluted when a cell divides. T cells were activated using PHA and IL-2, left to divide for 2 days, and then some T cells were replated onto LSSCs and restimulated, or replated and restimulated without LSSCs, or replated without restimulation. Histograms depict T cells, identified through expression of the T cell antigen receptor. Ratios indicate the proportion of LSSCs to T cells.
Figure 12:
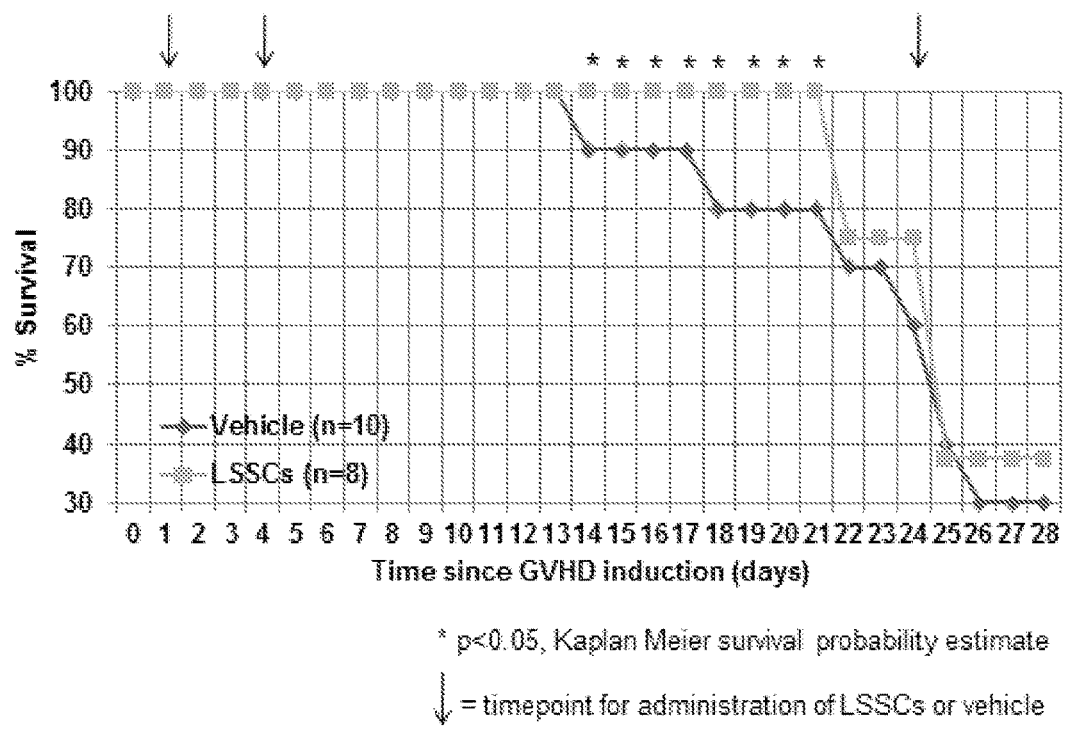
FIG. 12 shows that human LSSCs significantly reduce early lethality in mice with severe graft-versus-host disease. Recipient mice received an allogenic bone marrow transplant (split-dose lethal irradiation followed by i.v. injection of whole bone marrow). Severe GVHD was induced at the time of transplant by co-injecting donor derived splenocytes containing alloreactive T cells. $1 \times 10^6$ human LSSCs were injected intra-peritoneally at timepoints following GVHD induction, while control mice received saline (vehicle). Survival was monitored.

PDPN+ LSSC PDPN− LSSC, or unfractionated LSSC were cultured with freshly isolated, purified human blood-derived T cells from an unrelated donor. T cells were labeled with CFSE, which is diluted when a cell divides. T cells were activated using PHA and IL-2, left to divide for 2 days, and then some T cells were replated onto LSSCs and restimulated, or replated and restimulated without LSSCs, or replated without restimulation. FIG. 11 shows histograms depicting T cells, identified through expression of the T cell antigen receptor. Ratios indicate the proportion of LSSCs to T cells.

It was found that T cells that have been stimulated for 2 days, and then replated and restimulated with LSSCs, cease cell division, despite the fact that they have been fully activated and have gone through several cell divisions prior to replating (shown with the "replated, not restimulated" control). Both PDPN+ and PDPN− LSSC subpopulations are equally capable of suppressing pre-activated allogeneic T cells.

LSSCs Significantly Reduce Early Lethality in Mice with Severe Graft-Versus-Host Disease Recipient mice received an allogenic bone marrow transplant (split-dose lethal irradiation followed by i.v. injection of whole bone marrow). Severe GVHD was induced at the time of transplant by co-injecting donor derived splenocytes containing alloreactive T cells. $1 \times 10^6$ human LSSCs were injected intra-peritoneally at timepoints following GVHD induction, while control mice received saline (vehicle). Survival was monitored.

All mice developed GVHD at similar timepoints, however mice receiving LSSCs showed significantly reduced GVHD-associated lethality at early timepoints, suggesting that LSSCs reduce immune attack. The effects of early LSSC administration persisted for 3 weeks post-injection, at which point protection became ineffective, suggesting that re-administration may be indicated. A late injection of LSSCs (day 24) administered to severely affected mice did not reverse morbidity or mortality.

Figure 15:
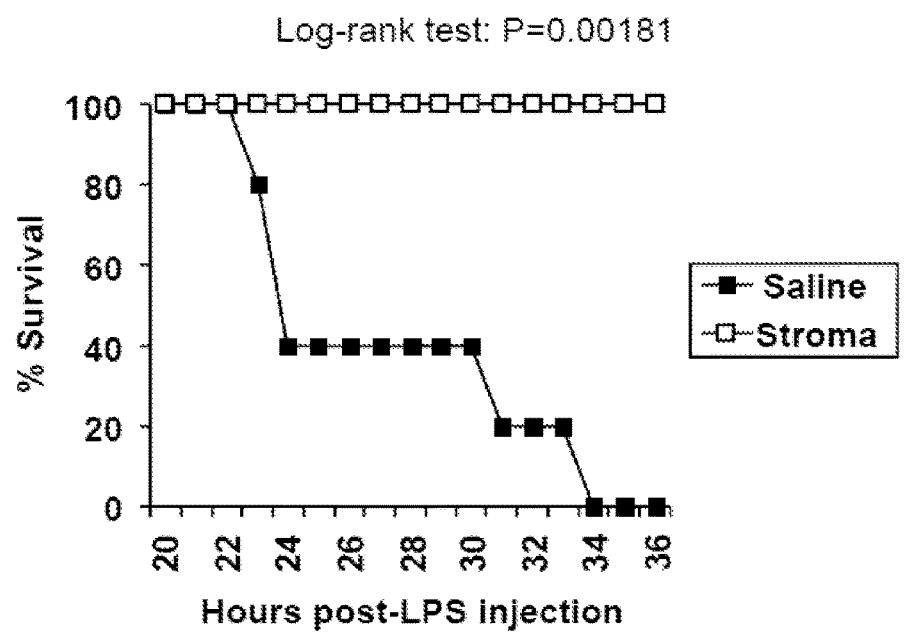
FIG. 15 shows that ex vivo expanded mouse lymph node stroma reduce the lethality of acute septic shock.
Figure 16A:
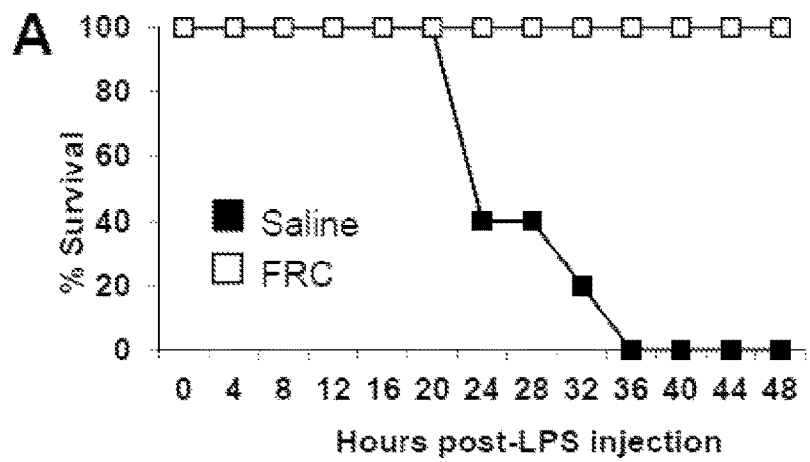
In FIG. 16A, young C57Bl6/J mice aged 3-6 weeks were treated with a LD100 dose of LPS, which is a polysaccharide that forms part of a bacterial cell wall, and which elicits a strong systemic immune response. As there is no active infection in this model, this model is known as "sterile sepsis". 4 hours after mice received LPS, they were treated with either FRCs in saline, or saline as a control. The graph depicts % survival over time.
Figure 16B:
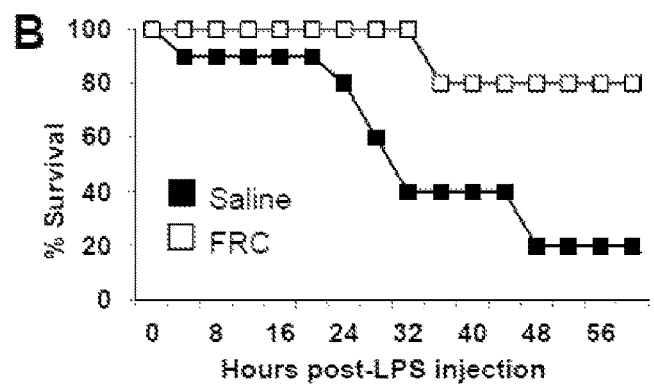
In FIG. 16B, sterile sepsis was induced in extremely old mice (18-24 months) as detailed in FIG. 16A, followed by either FRCs or saline 4 hours later. Survival was monitored.
Figure 16C:
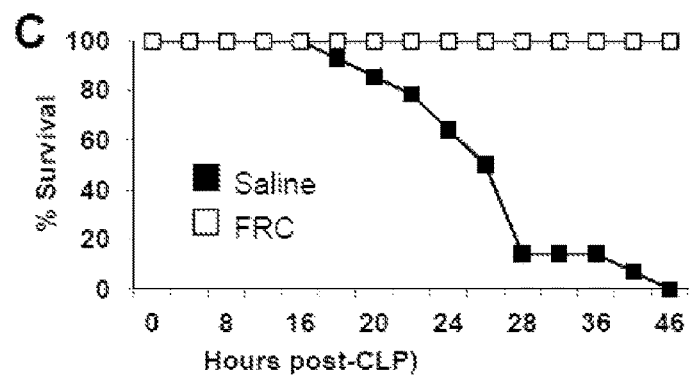
In FIG. 16C, young mice were given cecal ligation and puncture (CLP) sepsis, which involves puncturing the gut twice with a needle to allow spillage of fecal matter into the peritoneal cavity, setting up a severe infection which progresses to blood sepsis within 24 hours. This model mimics a burst appendix, gunshot wound, or other trauma to the gut). Autologous FRCs were administered 4 hours after CLP.
Figure 16D:
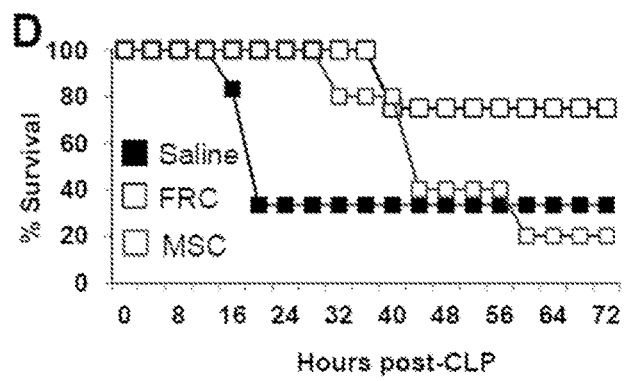
In FIG. 16D, young mice were given CLP sepsis and treated with antibiotics. Mice received saline, allogeneic FRCs or allogeneic MSCs as indicated 4 hours after CLP. MSCs (mesenchymal stromal cells) were used as a cell-based negative control.
Figure 16E:
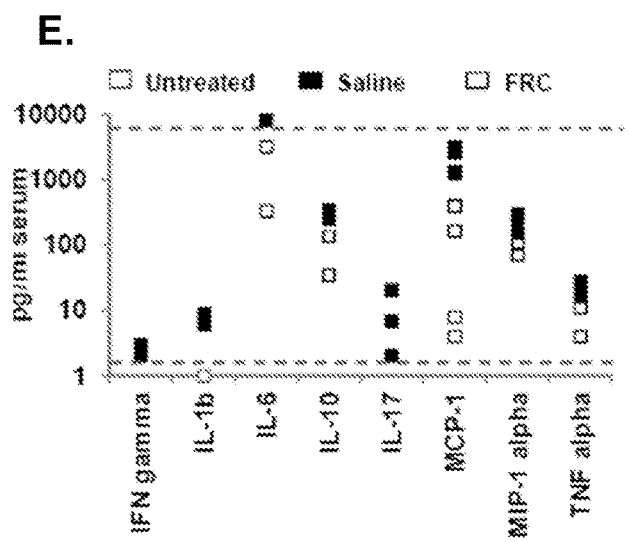
In FIG. 16E, mice in FIG. 16D were assessed 16 hours after CLP. Concentrations of key cytokines in blood plasma were measured, comparing mice that received saline or allogeneic FRCs and untreated (nonseptic) mice. Dotted lines represent the lower and upper limits of reliable detection.

As shown in FIG. 15, ex vivo expanded mouse lymph node stroma reduced the lethality of acute septic shock in mice.

Transcriptional Characteristics of LSSCs

Figure 13:
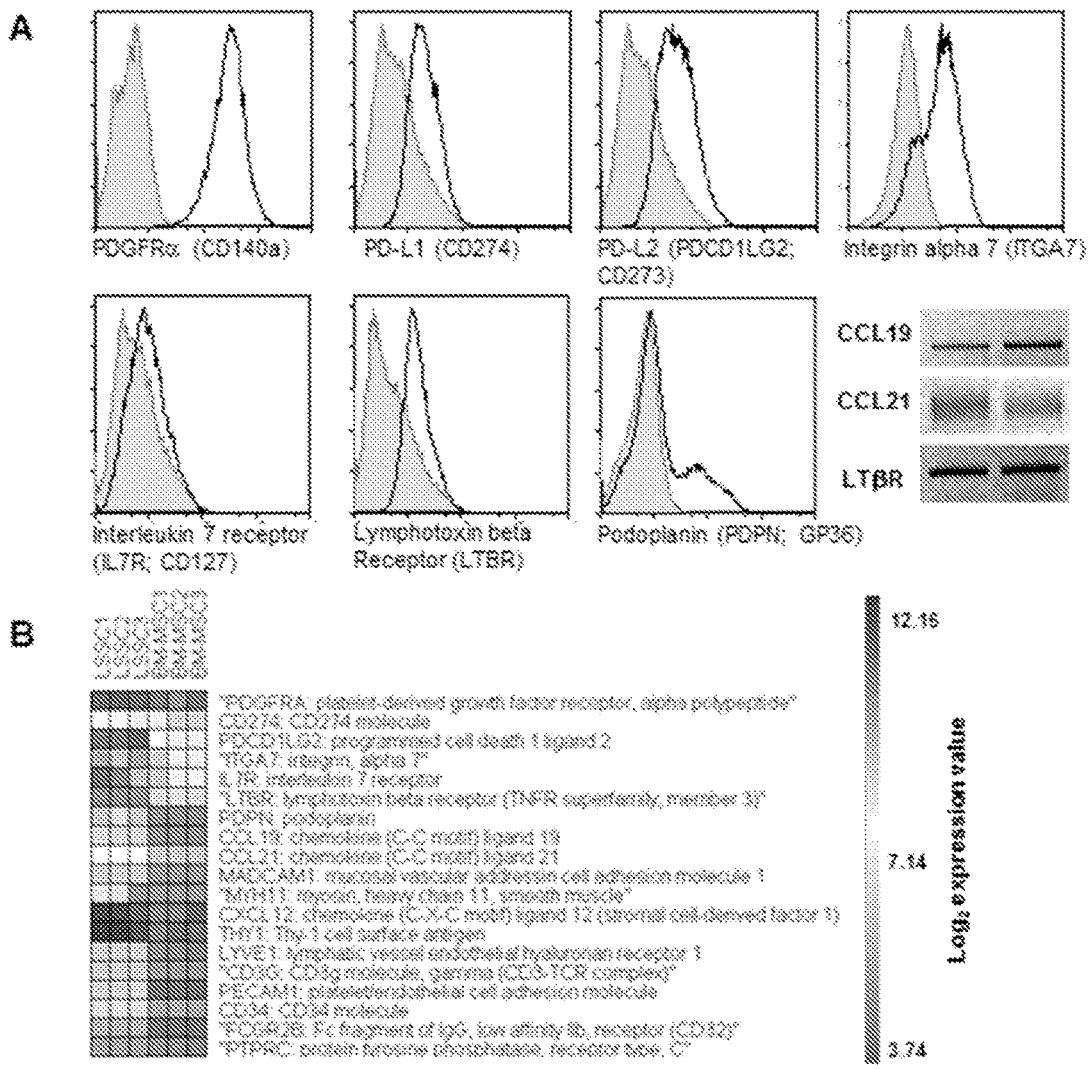
FIG. 13 shows that transcriptional characteristics of LSSCs. Transcriptional characteristics of human LSSCs were obtained using flow cytometry for surface markers and RT-PCR for secreted factor (FIG. 13A), and Affymetrix HuGene ST1.0 gene arrays to obtain mRNA transcriptomes (FIG. 13B).

Transcriptional characteristics of human LSSCs were obtained using flow cytometry for surface markers and RT-PCR for secreted factor (FIG. 13A), and Affymetrix HuGene ST1.0 gene arrays to obtain mRNA transcriptomes (FIG. 13B).

Representative flow cytometry profiles (FIG. 13A) of LSSCs (black line) compared to a relevant negative staining control (gray) showing expression of mesenchymal marker PDGFRa, tolerance associated proteins PD-L1 and PD-L2, muscle-associated protein ITGA7, and proteins characteristic of lymphoid organ stroma: LTBR, IL7R, and PDPN. PDPN and ITGA7 were likely expressed by a subset of bulk LSSCs. Alternate or gene names are shown in brackets. RT-PCR showed that LSSCs express transcript for chemokines CCL19 and CCL21 (shown relative to LTbR as a positive control).

Using a gene array, we also assessed transcription of selected genes from 3 LSSC samples, compared with publicly available data for 3 human bone marrow mesenchymal stem cell samples (accession codes GM241199, GM241201, GM241203). The data (FIG. 13B) showed that LSSCs expressed high levels of PD-L2, LTbR, Itga7, Myh11 compared to BM-MSCs. LSSCs and MSCs expressed similar levels of CXCL12, Thy1, IL7R, and were similarly negative for lineage-specific markers such as LYVE1, CD3G, PECAM1 (CD31), CD34, FCGR2B, and PTPRC (CD45). It has previously been reported that MSCs do not express PD-L2, nor can this protein be induced by exposure to inflammatory cytokine IFNg.

Morphological Characteristics of LSSCs

Figure 14:
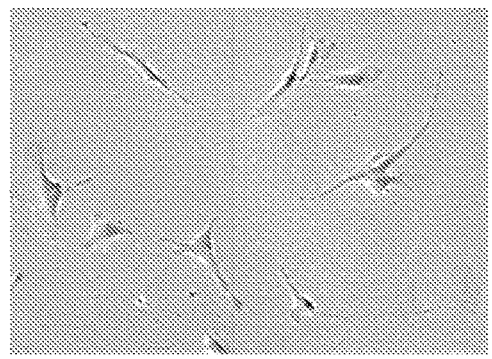
FIG. 14 shows the morphological characteristics of human LSSCs. Cultured LSSCs grown in alpha-MEM supplemented with fetal calf serum showed fibroblast-like morphology. They often exhibit long processes, lamellopodia, filopodia, ruffled leading edges, and focal adhesions. Original magnification: 100×.
Figure 19:
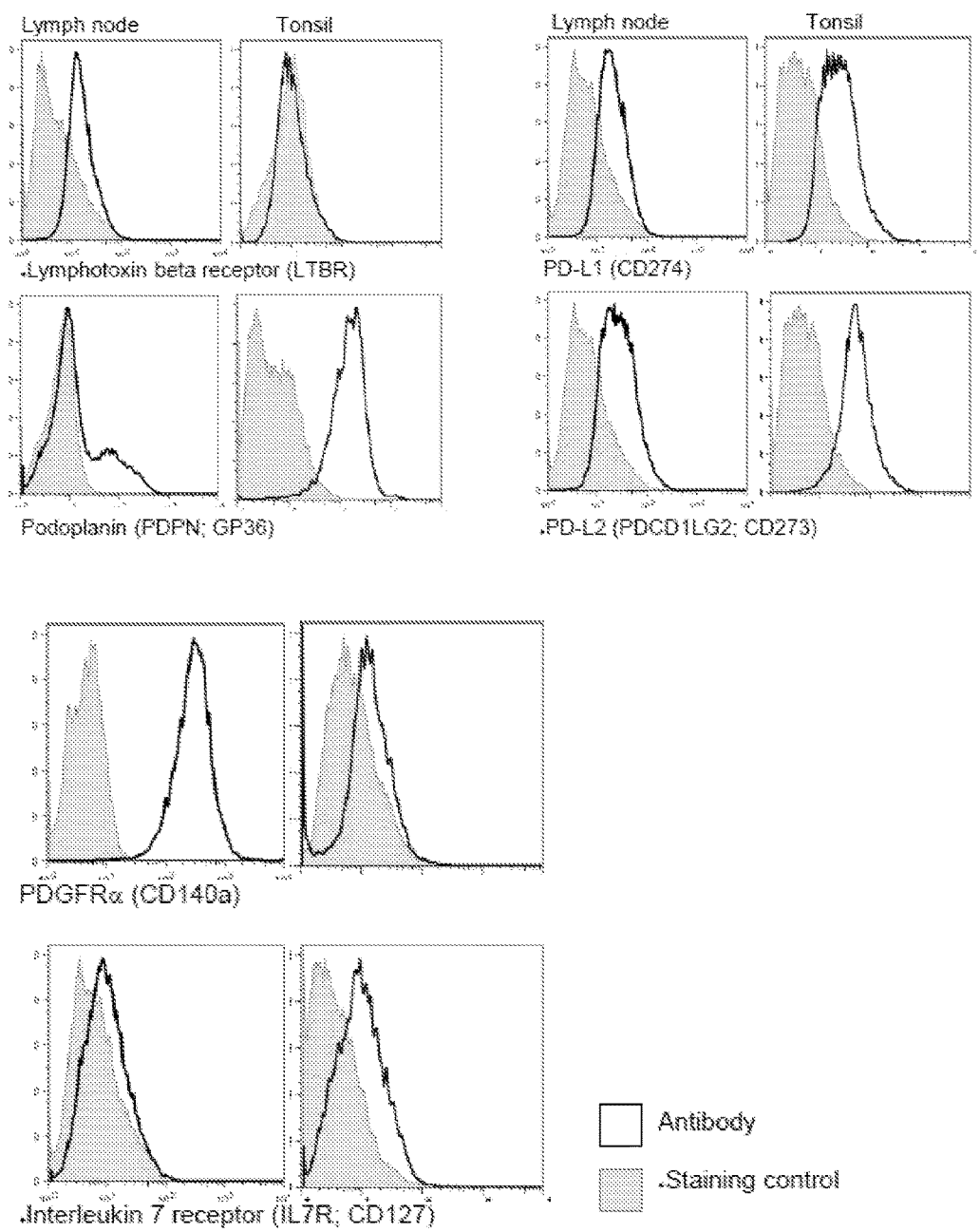
FIG. 19 demonstrates that LSSCs isolated from lymph node and tonsil are phenotypically similar. Human LSSCs derived from lymph node or tonsil were assessed by flow cytometry for surface expression of identifiers. All cells are CD45 negative, and CD31 negative.

Cultured LSSCs grown in alpha-MEM supplemented with fetal calf serum showed fibroblast-like morphology (FIG. 14). They often exhibit long processes, lamellopodia, filopodia, ruffled leading edges, and focal adhesions. Moreover, LSSCs isolated from lymph node and tonsil are phenotypically similar (FIG. 19).

FRCs Protect Against Sepsis in 2 Difference Mouse Models when Administered at Therapeutic Time Points.

Both in the sterile sepsis model and in the cecal ligation and puncture (CLP) sepsis model, FRCs imparted a significant survival benefit (FIG. 16). FIG. 16E shows reduced levels of inflammatory cytokines in the blood of FRC-treated mice. These inflammatory cytokines are usually associated with the innate immune system. Thus, FRCs interact with the innate immune system in sepsis.

FRCs Protect Against Colitis Mortality.

Figure 17:
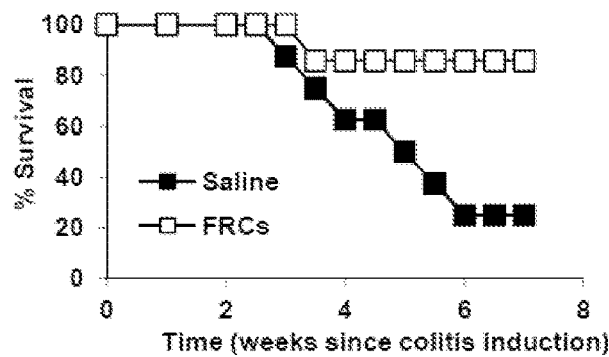
FIG. 17 shows that murine FRCs protect against colitis mortality. Colitis was induced by injecting purified naïve T cells into immunodeficient mice. The mice develop T cell-mediated inflammation against an unknown antigen (as happens in human disease), resulting in significant weight loss, hypertrophy of the colon, and mortality. This is a model for human chronic colitis or Crohn's disease. Allogeneic FRCs were administered at 2 weeks, after the mice started showing signs of illness and losing significant weight (a therapeutic timecourse). FRCs were injected twice weekly from week 2 to week 6 compared to saline-treated controls. Survival was monitored.

Colitis was induced by injecting purified naïve T cells into immunodeficient mice. Allogeneic FRCs were administered at 2 weeks, after the mice started showing signs of illness and losing significant weight (a therapeutic timecourse). FRCs were injected twice weekly from week 2 to week 6 compared to saline-treated controls, and survival was monitored. FRCs imparted a significant survival benefit (FIG. 17).

Human LSSCs Secrete Soluble Cytokine Factors and Cells Isolated from Lymph Node and Tonsil Show Comparable Levels of T Cell Suppression Via Soluble Factors.

Figure 18:
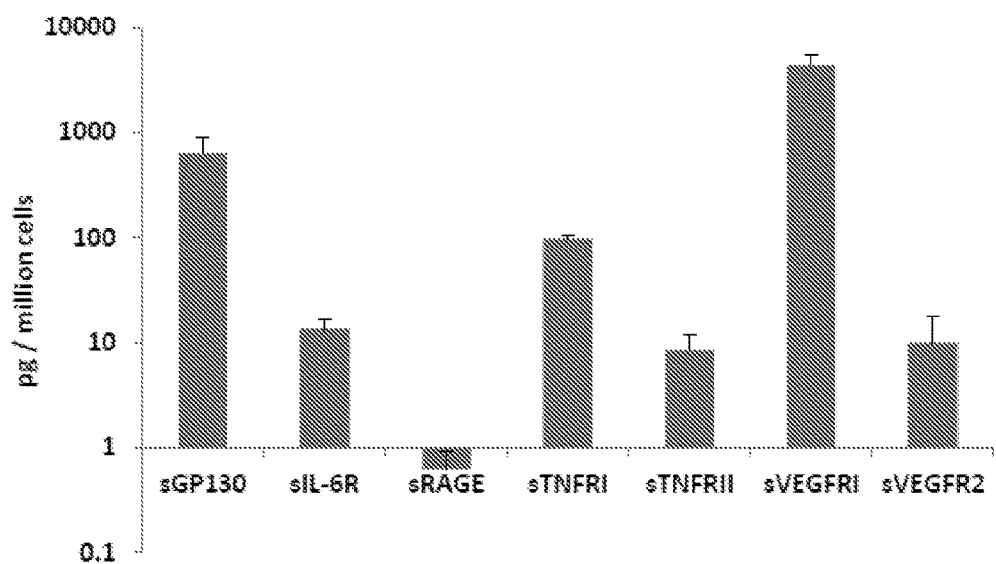
FIG. 18 shows that human LSSCs secrete soluble cytokine receptors. Human LSSCs were cultured in DMEM with BSA, without stimulation or addition of exogenous factors. Soluble cytokine receptor protein was detected from culture media 23 hours after plating, using the Luminex Corporation's MAGPIX system as per the manufacturer's instructions. Soluble cytokine receptors can bind free cytokines and prevent them from pro-inflammatory functions in vivo.
Figure 20:
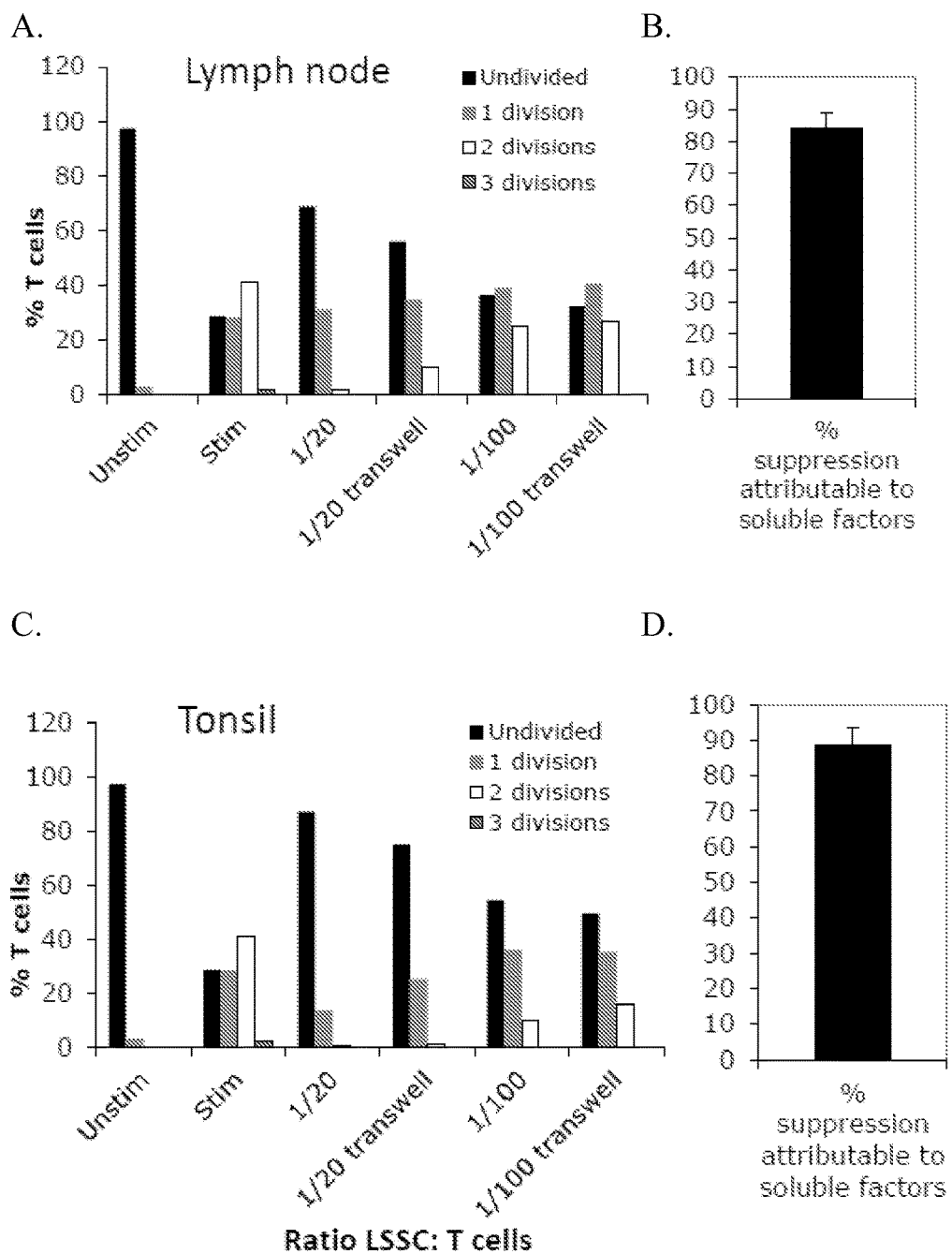
FIG. 20 shows that LSSCs isolated from lymph node (FIG. 20A and FIG. 20B) and tonsil (FIG. 20C and FIG. 20D) show comparable levels of T cell suppression via soluble factors. Allogeneic T cells derived from human blood were labeled with CFSE, which is diluted each time a cell divides. T cells were then activated using PHA and hIL-2, in the presence or absence of hLSSCs isolated from lymph node or tonsil. hLSSCs were present either within the well, or physically separated from the T cells by a 0.4 µm transwell membrane which allows soluble factors to pass through but not cells. Shown is the % T cells that have divided once, twice, 3 times, or not at all when incubated at different ratios of hLSSCs to T cells, with and without a transwell. % suppression due to soluble factors was calculated as: T cells divided with a transwell/T cell divided without a transwell×100.

Cultured human LSSCs were shown to secrete a number of soluble cytokine factors (FIG. 18). LSSCs isolated from lymph node and tonsil showed comparable levels of T cell suppression via soluble factors (FIG. 20).

Discussion

Techniques routinely employed in immunology and cell biology, such as generating viable single cell suspensions of reproducible composition from primary tissues, have created difficulties when applied to lymph node stroma. As such, histology and whole-organ PCR, or in vivo systems involving lymphocytic readouts have been the field's standard. These have led to several important advances regarding the role of lymph node stromal cell subsets in steady-state tolerance and immunity; however, there are many unexplored questions of direct biological and medical relevance. We believe that modern immunological and cell biological techniques, refined and adapted for use with these rare and delicate cell types, will be required to answer these.

Highlighting this unmet need, DN stroma in particular remain almost completely undefined. Several groups have now reported the existence of this non-hematopoietic stromal cell subset (which may or may not be homogeneous) (Link et al., 2007, Cohen et al., 2010, Fletcher et al., 2010) but despite comprising >10% of the lymph node stromal niche and harboring an Aire-expressing cell type (Cohen et al., 2010, Fletcher et al., 2010), it has remained almost entirely uncharacterized. Such fundamental characteristics as morphology, lineage, surface phenotype, and function are unreported. These deficits speak directly to the difficulties inherent in studying lymph node stromal cells.

One such difficulty in studying DN cells is that dying or poorly stained lymphocytes appear CD45 low or negative, appearing in the stromal cell gate with the same phenotype (CD31$^-$podoplanin$^-$) as DN stroma. This greatly skews the proportions of true stromal subsets, making it difficult to tie down even the most basic proportional composition of the lymph node stromal niche. Indeed, since stroma comprise only 1-2% of lymph node cells, non-viable lymphocytes routinely outnumber stroma even in a highly viable (>95% live) single cell suspension. In our experience, inclusion of a dead cell stain such as propidium iodide, does not adequately remove cells that appear CD45-low post-digestion.

For this reason, we felt that the key to reproducible isolation of stroma lay in developing a low-mortality enzymatic digestion protocol. Using a combination of dispase, DNase I and collagenase P, we routinely isolated a high number of stromal cells with >95% viability. This also allowed us to compare each stromal subset across individual mice and humans, and to successfully sort rare subsets, including DN cells and MRCs, which will be the subject of further study. It has not yet been possible to identify DN stroma by histology, since no unique or differentially expressed surface markers are reported. However, the sorting strategy described herein could be used to perform the unbiased array-based approaches required to unmask this rare subset.

Similarly, these methods allowed us to isolate the four major populations of human lymph node stromal cells directly from primary tissue, opening the door for sophisticated clinical and pre-clinical studies. It is now well established that mouse lymph node stromal cells express many clinically relevant self-antigens and directly present these to T cells to tolerize them (Lee et al., 2007, Nichols et al., 2007, Gardner et al., 2008, Magnusson et al., 2008, Cohen et al., 2010, Fletcher et al., 2010). It is possible that the same mechanisms may be at play in humans. Studies have shown that FRCs and LECs retain the ability to present PTAs to naïve T cells while in culture, mimicking interactions seen in vivo (Cohen et al., 2010, Fletcher et al., 2010), though it is unclear whether this is due to continual transcription of the PTAs in question, or retention of peptide-MHC. These techniques could be used to address this and many other outstanding questions pertaining to human lymph node biology.

Further, the development of 3D culture systems for lymph nodes will allow the creation of highly controlled experimental systems mimicking conditions and interactions in vivo. We found that DCs and lymphocytes readily and preferentially migrated on FRC networks in vitro, as has been observed in vivo. Such techniques are particularly applicable to studies with human cells.

We found strikingly low variation in stromal cell subsets between young male age-matched C57Bl/6 mice. In testing whether cross-talk between lymphocytes and stroma was required for the expansion of particular stromal subsets, we found that FRCs, LECs, BECs and DN stroma were present at normal proportions in Rag$^{-/-}$ mice, showing no requirement for T or B cells in their development or expansion. The MRC (MadCAM-1$^+$) stromal subset has not previously been isolated for flow cytometric analysis, and we found that MRCs formed a subset within the podoplanin$^+$ CD31$^-$ FRC gate. While MRCs show similarities to FRCs, expressing VCAM-1 and ICAM-1, and secreting ECM components such as laminin, they additionally produce high amounts of CXCL13 and can be identified through expression of Mad-CAM-1 (Katakai et al., 2008)

Strikingly, the number of MRCs was significantly reduced in Rag$^{-/-}$ mice. The level of MadCAM protein per cell was also lower. By histology, MadCAM+ MRCs are visible in skin-draining Rag$^{-/-}$ lymph nodes (Katakai et al., 2008), however numerical and quantitative flow cytometric analysis of MadCAM expression and MRC numbers has not previously been possible. These data suggest that lymphocytes are indeed required for normal development of MRCs. Interestingly, LECs from Rag$^{-/-}$ mice also developed into MadCAM+ cells at reduced proportions, and showed less protein per cell. It is as yet unclear whether MRCs and MadCAM+ LECs fail to expand normally in Rag$^{-/-}$ mice, or just fail to upregulate MadCAM. The role for MadCAM+ LECs is also undescribed.

Since MRCs show the same phenotype as LTo cells (Katakai et al., 2008), which construct the lymph node downstream of lymphotoxin signaling and an NF-κB2 transcription program (Mebius, 2003, Coles et al., 2010), it has been postulated that MRCs may play a role in post-natal maintenance or regeneration of the lymph node stroma (Katakai et al., 2008). Our results show that normal expansion and/or maturation of MadCAM+ MRCs is not required for normal expansion of FRCs, BECs and DN stroma. However, further functional studies would be required to determine if MRC function (expression of chemokines, for example) and MadCAM expression were inexorably linked.

An unexpected finding was that the FRCs of skin-draining and mesenteric lymph nodes significantly differed in proportion, number, and transcriptional profile. We found significantly fewer FRCs in mesenteric lymph nodes, containing reduced expression of several important cytokines and chemokines: IL6, IL7, BAFF, CXCL9, CXCL10, IL1 receptor accessory protein (IL1RAP), Activin receptor IIA, VEGFa, LIF, and cKIT-ligand. Statistically, the pathway analysis showed that these genes were highly unlikely to have clustered by chance. It will be interesting to determine whether these changes occur as the result of a congenital developmental difference, or following exposure to different inflammatory cues, such as differences in antigen exposure frequency or dose. Skin-draining and mesenteric lymph nodes are exposed to markedly different microenvironmental stimuli. Unless skin barriers are breached, FRCs residing in skin-draining lymph nodes from this study could be expected to encounter large doses of microbe-sourced antigen relatively rarely. Mesenteric FRCs, however, are constantly exposed to a barrage of pathogen-associated molecular patterns through normal functioning of the gut, with important steady-state roles in Treg induction and oral tolerance (Hadis et al., 2011). These day-to-day factors are reasonably be expected to alter expression profile, to unknown effect.

Developmental differences in skin-draining lymph nodes and mesenteric lymph nodes have been reported: a full complement of mesenteric lymph nodes are present in Cxcl13−/− and Cxcr5−/− mice, while many skin-draining lymph nodes are missing, or develop variably in particular locations (Ansel et al., 2000). Similarly, Ltb−/− mice develop mesenteric lymph nodes (albeit abnormally) but lack many skin-draining lymph nodes (Koni et al., 1997). Since lymph node development is initiated during embryogenesis, these results suggest that cytokines capable of compensating for CXCL13 or LTβ are more highly available in prenatal mesenteric lymph nodes than skin-draining lymph nodes. Similarly, a lower proportion of presumptive lymph node organizer cells are present in the skin-draining lymph nodes of neonates compared with mesenteric lymph nodes (Cupedo et al. J Imm 2004). Finally, after transplanting skin-draining lymph nodes to the mesentery, it was found that MadCAM$^-$ BECs do not adopt the mesenteric MadCAM+ phenotype, suggesting the difference is developmental and not a result of exposure to gut-derived antigens (Ahrendt et al., 2008). A recent study also interestingly suggests that stroma from transplanted peripheral and mesenteric lymph nodes may differ in their ability to induce oral tolerance, assuming that carryover hematopoietic cells, progressively replaced by donor cells after transplant, are not influential (Buettner et al., 2011).

In the skin-draining lymph nodes of 6 week old mice, we found higher expression of several cytokines with known roles in lymph nodes. IL6, upregulated 6-fold in FRCs from skin-draining lymph nodes, is a cytokine subject to complex regulation. When produced early in the immune response after exposure to pro-inflammatory IL1, IL6 is potently immunostimulatory, but can also exert anti-inflammatory functions through dampening of TNFα and IL-1 signaling, and upregulation of IL10. IL10 was not expressed by stroma (data not shown). Instead, we found >3-fold upregulation of the IL1 receptor accessory protein (IL1Rap) in skin-draining lymph nodes, suggesting that skin-draining lymph node FRCs possess the capacity to increase IL6 production early in infection. Accordingly, during steady-state, FRCs from skin-draining lymph nodes also expressed high levels of IL1R1, the high-affinity binding partner of IL1Rap, and did not express the decoy analog IL1-RN (Dinarello, 1996) (data not shown). Supporting these findings, we have previously reported that FRCs respond to TLR3 signaling within hours (Fletcher et al., 2010), suggesting that FRCs respond swiftly to infection. It is also worth noting that IL6 is produced in an anti-inflammatory capacity by smooth muscle cells following stretch (Pedersen, 2006), as a means of phosphorylating PDGF-receptors and stimulating cell contraction (Hu et al., 1998, Zampetaki et al., 2005). Similarly, in dermal myofibroblasts, IL6 modulates alpha smooth muscle actin to enhance contraction and wound closure (Gallucci et al., 2006). Like myofibroblasts, FRCs are highly contractile cells expressing large amounts of alpha smooth muscle actin ((Link et al., 2007) and data not shown). IL6 shares a receptor with LIF, which was also upregulated in FRCs from skin-draining lymph nodes. Like IL6, LIF is upregulated in contracting myocytes as a means of inducing autocrine or paracrine muscle cell proliferation. IL6, IL1Rap and LIF represented the 3 genes most upregulated by FRCs from skin-draining lymph nodes in the identified network.

With direct relevance for lymphocyte function, we found that IL7 and BAFF were upregulated by more than twofold in skin-draining FRCs. IL7 is a known product of FRCs, and functions to maintain naïve T cells (Link et al., 2007). BAFF is a potent survival factor and costimulatory activator for B cells. In secondary lymphoid organs, it is known to be produced by non-hematopoietic FDCs, but has not previously been reported in FRCs. However, the expression of BAFF by stromal cells outside lymph nodes is well-reported, though this seems to require chronic inflammation and has not previously been linked to steady-state stroma (Mackay et al., 2009). Our cell sorts did not contain FDC contamination, since during transcriptional analysis, we found no evidence for expression of Fcγ receptors, and <1% of lymph node stromal cells stain positive for FDC-M1 or CD35 (data not shown). FDCs are confined to the B cell follicle, while FRCs surround, and occasionally extend into the B cell follicle. However, both cell types are thought to develop from a common precursor (Mebius, 2003). This result supports and extends the list of noted similarities between these cell types.

Strikingly, our results indicated that CXCL9 and CXCL10 are expressed by FRCs in skin-draining and mesenteric lymph nodes. These chemokines both signal through CXCR3, expressed by activated T cells, B cells and NK cells, and their transcription is upregulated by IFNγ, IFNα, and other proinflammatory stimuli (Muller et al., 2010). While a role for CXCL10 in lymph nodes during steady-state has not been described, during some infections CXCL10 has an important role retaining Th1 lymphocytes in lymph nodes, a mechanism which encourages newly activated T cells to also become Th1, creating a polarized, microbe-appropriate response (Yoneyama et al., 2002). However, to date, CXCL10 production has only been identified in mature DCs within lymph nodes (Yoneyama et al., 2002). These data show that CXCL10 mRNA is also expressed by steady-state FRCs, with unknown function.

CXCL9 is poorly studied, but has been observed in dendritic cells from cancer-associated lymphoid tissues and draining lymph nodes (Ohtani et al., 2009), Any role in steady-state regulation of cell migration in lymph nodes is unreported.

Interestingly, FRCs from both mesenteric and skin-draining lymph nodes expressed genes involved in signaling to endothelial cells. It is known that FRCs are the primary producers of VEGF in skin-draining lymph nodes under steady-state conditions (Chyou et al., 2008). Surprisingly we found that FRCs from skin-draining lymph nodes expressed higher levels of VEGFa than those from mesenteric lymph nodes. Indeed, mesenteric lymph nodes showed upregulation of a relatively short list of genes compared to skin-draining lymph nodes, and the results did not map to a functional pathway when our robust statistical correction for multiple hypotheses was performed. However, we observed upregulation of known gut-related genes such as Nkx2-3, required for MadCAM expression and lymphocyte segregation in mesenteric lymph nodes (Pabst et al., 2000); as well as upregulation of Lrat, Tgm2, Meis1 and Pltp. These genes are either involved in the retinoic acid metabolism cycle, or upregulated by retinoic acid, (Matsuura et al., 1993, Cao et al., 2002, Galdones et al., 2006, Rebe et al., 2009) which is processed in mesenteric lymph nodes to impose a gut-specific homing phenotype on T cells (Iwata, 2009). We also found expression of several vasodilators (Vipr2, Itih4, Npr1) and a vasoconstrictor (Agt) suggesting that FRCs actively communicate with lymph node blood vessels. Similarly, upregulation of genes that induce neurite outgrowth (Efna5, gpr126, Tmem35 and Ngf) suggests a potential role in maintaining the normal sympathetic innervation of the lymph node (Panuncio et al., 1999). Further studies would be required to validate these results.

Taken together, altered expression of cytokines and chemokines in skin-draining lymph nodes suggests a novel picture of microenvironmental regulation by FRCs. Expression of BAFF and CXCR3 ligands imply previously unreported mechanisms of cross-talk with the hematopoietic system. Similarly, the upregulation of IL-6, IL1Rap, and LIF suggests that skin-draining lymph node FRCs may be more contractile, and/or actively dividing faster than their mesenteric lymph node counterparts, similarly influencing endothelial cells to keep pace by transcribing increased VEGFα.

These transcriptional events may not be occurring equally across all FRCs, however. Lymph nodes contain a number of poorly understood FRC microniches. The best studied of these is the cortical T cell zone FRC, (sometimes called a TRC), which produces IL-7, CCL19, CCL21, maintains the conduit system, and is used as a scaffold for the migration of DCs, T cells and B cells. However, fibroblastic gp38+ CD31⁻ cells exist throughout the lymph node: in the subcapsular region abutting B cell follicles; as pericytes; and throughout the medulla. It is not yet possible to differentiate between these different FRC types, and the differences between skin-draining lymph nodes and mesenteric lymph nodes may involve a change in their proportion, if they differentially express the cytokines and chemokines identified.

Together, these data represent a comprehensive catalog of techniques adapted for lymph node stromal cells.

TABLE 1

A sample range of low-pressure stromal sorting parameters for 100 μm tip in the FACSAria and FACSAria IIu (BD Biosciences). n = 4-8 independent experiments

| Sort Parameter | FACSAria | FACSAria IIu |
| --- | --- | --- |
| Frequency | 23.1-25.9 | 19.2-21.6 |
| Amplitude | 24.0-45.6 | 8.6-13.5 |
| Phase | 0-3 | 0 |
| Attenuation | On | Off |
| Drop Delay | 18.56-20.81 | 15.96-17.92 |
| First Drop | 189-295 | 200-243 |
| Target Gap | 6-10 | 10 |

TABLE 2

Enzyme sensitivity of surface markers used to characterize non-hematopoietic lymph node stromal cells. Cultured or freshly isolated stroma were incubated with enzymes for 10 mins, then surface protein expression tested by flow cytometry. Data represent n = 3 independent experiments

| Surface Marker | Collagenase P | Dispase | Trypsin |
| --- | --- | --- | --- |
| CD31 | + | + | − |
| CD40 | + | + | +/− |
| CD44 | + | + | + |
| CD45 | + | + | + |
| CD80 | + | + | − |
| CD140a | + | + | − |
| ICAM-1 | + | + | + |
| Gp38 | + | + | + |
| Thy-1 | + | + | +/− |
| PD-L1 | + | + | + |
| Sca-1 | + | + | + |
| Lyve-1 | + | + | + |
| VCAM-1 | + | + | + |
| MadCAM | + | + | + |

+ Surface marker present (not sensitive)
− Surface marker absent (sensitive)
+/− Surface marker partially cleaved (partially sensitive)

TABLE 3

Genes upregulated in FRCs from mesenteric lymph nodes compared to FRCs from skin-draining lymph nodes, grouped by functional similarity. Gene expression of sorted FRCs from skin-draining or mesenteric lymph nodes was compared using microarray analysis. Gene selection was based on expression (mean expression of >120 in either SLN or MLN), a low coefficient of variance between replicates (<0.05), fold-change (at least 2 fold increased in mesenteric lymph node FRCs compared to skin-draining FRCs) and P-value (* <0.05; ** <0.01; student's T test). Genes were grouped based on literature keyword searches.

| Functional group | Gene | Fold-change | P-value |
|---|---|---|---|
| Regulation of cell growth in fibroblasts | Wnt2b | 8.13 | ** |
| | Slit2 | 6.06 | ** |
| | Sfrp4 | 3.13 | ** |
| | Wfdc1 | 2.77 | ** |
| | Mest | 2.60 | * |
| | Dhcr24 | 2.48 | ** |
| | Fgfr3 | 2.39 | ** |
| | Igfbp6 | 2.20 | * |
| | Figf | 2.17 | ** |
| | Bmp2 | 2.12 | ** |
| Induced by gut-specific factors | Nkx2-3 | 5.75 | ** |
| | Lrat | 4.67 | ** |
| | Tgm2 | 2.66 | ** |
| | Enpp3 | 2.48 | * |
| | Kcnn3 | 2.24 | * |
| | Meis1 | 2.13 | ** |
| | Pltp | 2.07 | ** |
| Extra-cellular matrix or cell-cell junction interactions | Mfap5 | 3.38 | * |
| | Hmcn2 | 2.69 | ** |
| | Gpc3 | 2.34 | ** |
| | Itih4 | 2.34 | ** |
| | Cldn10 | 2.32 | ** |
| | Col14a1 | 2.26 | ** |
| | Loxl1 | 2.25 | ** |
| | Cilp | 2.01 | * |
| Endothelial or pericyte cross-talk | Ptgs1 | 3.17 | ** |
| | Vipr2 | 2.92 | ** |
| | Smoc2 | 2.79 | * |
| | Itih4 | 2.34 | ** |
| | Npr1 | 2.33 | * |
| | Figf | 2.17 | ** |
| | Agt | 2.03 | ** |
| Neuronal cross-talk | Efna5 | 2.58 | ** |
| | Gpr126 | 2.22 | ** |
| | Tmem35 | 2.04 | ** |
| | Ngf | 2.00 | ** |

This invention is not limited in its application to the details of construction and the arrangement of components set forth in the above description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

REFERENCES

Ahrendt, M., Hammerschmidt, S. I., Pabst, O., Pabst, R., and Bode, U. (2008). Stromal cells confer lymph node-specific properties by shaping a unique microenvironment influencing local immune responses. J Immunol 181, 1898-1907.

Ansel, K. M., Ngo, V. N., Hyman, P. L., Luther, S. A., Forster, R., Sedgwick, J. D., Browning, J. L., Lipp, M., and Cyster, J. G. (2000). A chemokine-driven positive feedback loop organizes lymphoid follicles. Nature 406, 309-314.

Bajenoff, M., Egen, J. G., Koo, L. Y., Laugier, J. P., Brau, F., Glaichenhaus, N., and Germain, R. N. (2006). Stromal cell networks regulate lymphocyte entry, migration and territoriality in lymph nodes. Immunity 25, 989-1001.

Buettner, M., Pabst, R., and Bode, U. (2011). Lymph node stromal cells strongly influence immune response suppression. Eur J Immunol 41, 624-633.

Cao, G., Beyer, T. P., Yang, X. P., Schmidt, R. J., Zhang, Y., Bensch, W. R., Kauffman, R. F., Gao, H., Ryan, T. P., Liang, Y., Eacho, P. I., and Jiang, X. C. (2002). Phospholipid transfer protein is regulated by liver x receptors in vivo. J Biol Chem 277, 39561-39565.

Chyou, S., Ekland, E. H., Carpenter, A. C., Tzeng, T. C., Tian, S., Michaud, M., Madri, J. A., and Lu, T. T. (2008). Fibroblast-type reticular stromal cells regulate the lymph node vasculature. J Immunol 181, 3887-3896.

Cohen, J. N., Guidi, C. J., Tewalt, E. F., Qiao, H., Rouhani, S. J., Ruddell, A., Farr, A. G., Tung, K. S., and Engelhard, V. H. (2010). Lymph node-resident lymphatic endothelial cells mediate peripheral tolerance via aire-independent direct antigen presentation. J Exp Med 207, 681-688.

Coles, M., Kioussis, D., and Veiga-Fernandes, H. (2010). Cellular and molecular requirements in lymph node and peyer's patch development. Prog Mol Biol Transl Sci 92, 177-205.

Cyster, J. G., Ansel, K. M., Reif, K., Ekland, E. H., Hyman, P. L., Tang, H. L., Luther, S. A., and Ngo, V. N. (2000). Follicular stromal cells and lymphocyte homing to follicles. Immunol Rev 176, 181-193.

Dennis, G., Jr., Sherman, B. T., Hosack, D. A., Yang, J., Gao, W., Lane, H. C., and Lempicki, R. A. (2003). David: Database for annotation, visualization, and integrated discovery. Genome Biol 4, P3.

Dinarello, C. A. (1996). Biologic basis for interleukin-1 in disease. Blood 87, 2095-2147.

Eikelenboom, P., Nassy, J. J., Post, J., Versteeg, J. C., and Langevoort, H. L. (1978). The histogenesis of lymph nodes in rat and rabbit. Anat Rec 190, 201-215.

Fletcher, A. L., Lukacs-Kornek, V., Reynoso, E. D., Pinner, S. E., Bellemare-Pelletier, A., Curry, M. S., Collier, A. R., Boyd, R. L., and Turley, S. J. (2010). Lymph node fibroblastic reticular cells directly present peripheral tissue antigen under steady-state and inflammatory conditions. J Exp Med 207, 689-697.

Fletcher, A. L., Malhotra, D., and Turley, S. J. (2011). Lymph node stroma broaden the peripheral tolerance paradigm. Trends Immunol 32, 12-18.

Galdones, E., Lohnes, D., and Hales, B. F. (2006). Role of retinoic acid receptors alpha1 and gamma in the response of murine limbs to retinol in vitro. Birth Defects Res A Clin Mol Teratol 76, 39-45.

Gallucci, R. M., Lee, E. G., and Tomasek, J. J. (2006). Il-6 modulates alpha-smooth muscle actin expression in dermal fibroblasts from il-6-deficient mice. J Invest Dermatol 126, 561-568.

Gardner, J. M., Devoss, J. J., Friedman, R. S., Wong, D. J., Tan, Y. X., Zhou, X., Johannes, K. P., Su, M. A., Chang, H. Y., Krummel, M. F., and Anderson, M. S. (2008). Deletional tolerance mediated by extrathymic aire-expressing cells. Science 321, 843-847.

Hadis, U., Wahl, B., Schulz, O., Hardtke-Wolenski, M., Schippers, A., Wagner, N., Muller, W., Sparwasser, T., Forster, R., and Pabst, O. (2011). Intestinal tolerance requires gut homing and expansion of foxp3+ regulatory t cells in the lamina propria. Immunity 34, 237-246.

Hu, Y., Bock, G., Wick, G., and Xu, Q. (1998). Activation of pdgf receptor alpha in vascular smooth muscle cells by mechanical stress. Faseb J 12, 1135-1142.

Irizarry, R. A., Hobbs, B., Collin, F., Beazer-Barclay, Y. D., Antonellis, K. J., Scherf, U., and Speed, T. P. (2003). Exploration, normalization, and summaries of high density oligonucleotide array probe level data. Biostatistics 4, 249-264.

Iwata, M. (2009). Retinoic acid production by intestinal dendritic cells and its role in t-cell trafficking. Semin Immunol 21, 8-13.

Junt, T., Scandella, E., and Ludewig, B. (2008). Form follows function: Lymphoid tissue microarchitecture in antimicrobial immune defence. Nat Rev Immunol 8, 764-775.

Katakai, T., Hara, T., Lee, J. H., Gonda, H., Sugai, M., and Shimizu, A. (2004a). A novel reticular stromal structure in lymph node cortex: An immuno-platform for interactions among dendritic cells, t cells and b cells. Int Immunol 16, 1133-1142.

Katakai, T., Hara, T., Sugai, M., Gonda, H., and Shimizu, A. (2004b). Lymph node fibroblastic reticular cells construct the stromal reticulum via contact with lymphocytes. J Exp Med 200, 783-795.

Katakai, T., Suto, H., Sugai, M., Gonda, H., Togawa, A., Suematsu, S., Ebisuno, Y., Katagiri, K., Kinashi, T., and Shimizu, A. (2008). Organizer-like reticular stromal cell layer common to adult secondary lymphoid organs. J Immunol 181, 6189-6200.

Koni, P. A., Sacca, R., Lawton, P., Browning, J. L., Ruddle, N. H., and Flavell, R. A. (1997). Distinct roles in lymphoid organogenesis for lymphotoxins alpha and beta revealed in lymphotoxin beta-deficient mice. Immunity 6, 491-500.

Lee, J. W., Epardaud, M., Sun, J., Becker, J. E., Cheng, A. C., Yonekura, A. R., Heath, J. K., and Turley, S. J. (2007). Peripheral antigen display by lymph node stroma promotes t cell tolerance to intestinal self. Nat Immunol 8, 181-190.

Link, A., Hardie, D. L., Favre, S., Britschgi, M. R., Adams, D. H., Sixt, M., Cyster, J. G., Buckley, C. D., and Luther, S. A. (2011). Association of t-zone reticular networks and conduits with ectopic lymphoid tissues in mice and humans. Am J Pathol 178, 1662-1675.

Link, A., Vogt, T. K., Favre, S., Britschgi, M. R., Acha-Orbea, H., Hinz, B., Cyster, J. G., and Luther, S. A. (2007). Fibroblastic reticular cells in lymph nodes regulate the homeostasis of naive t cells. Nat Immunol 8, 1255-1265.

Luther, S. A., Tang, H. L., Hyman, P. L., Farr, A. G., and Cyster, J. G. (2000). Coexpression of the chemokines elc and slc by t zone stromal cells and deletion of the elc gene in the plt/plt mouse. Proc Natl Acad Sci USA 97, 12694-12699.

Mackay, F., and Schneider, P. (2009). Cracking the baff code. Nat Rev Immunol 9, 491-502.

Magnusson, F. C., Liblau, R. S., von Boehmer, H., Pittet, M. J., Lee, J. W., Turley, S. J., and Khazaie, K. (2008). Direct presentation of antigen by lymph node stromal cells protects against cd8 t-cell-mediated intestinal autoimmunity. Gastroenterology 134, 1028-1037.

Matsuura, T., and Ross, A. C. (1993). Regulation of hepatic lecithin: Retinol acyltransferase activity by retinoic acid. Arch Biochem Biophys 301, 221-227.

Mebius, R. E. (2003). Organogenesis of lymphoid tissues. Nat Rev Immunol 3, 292-303.

Mei S H, Haitsma J J, Dos Santos C C, Deng Y, Lai P F, Slutsky A S, Liles W C, Stewart D J. Mesenchymal stem cells reduce inflammation while enhancing bacterial clearance and improving survival in sepsis. Am J Respir Crit Care Med. 2010; 182(8):1047-57.

Muller, M., Carter, S., Hofer, M. J., and Campbell, I. L. (2010). Review: The chemokine receptor cxcr3 and its ligands cxcl9, cxcl10 and cxcl11 in neuroimmunity—a tale of conflict and conundrum. Neuropathol Appl Neurobiol 36, 368-387.

Németh K, Leelahavanichkul A, Yuen P S, Mayer B, Parmelee A, Doi K, Robey P G, Leelahavanichkul K, Koller B H, Brown J M, Hu X, Jelinek I, Star R A, Mezey E. Bone marrow stromal cells attenuate sepsis via prostaglandin E(2)-dependent reprogramming of host macrophages to increase their interleukin-10 production. Nat Med. 2009; 15(1):42-9

Nichols, L. A., Chen, Y., Colella, T. A., Bennett, C. L., Clausen, B. E., and Engelhard, V. H. (2007). Deletional self-tolerance to a melanocyte/melanoma antigen derived from tyrosinase is mediated by a radio-resistant cell in peripheral and mesenteric lymph nodes. J Immunol 179, 993-1003.

Ohtani, H., Jin, Z., Takegawa, S., Nakayama, T., and Yoshie, O. (2009). Abundant expression of cxcl9 (mig) by stromal cells that include dendritic cells and accumulation of cxcr3+ t cells in lymphocyte-rich gastric carcinoma. J Pathol 217, 21-31.

Pabst, O., Forster, R., Lipp, M., Engel, H., and Arnold, H. H. (2000). Nkx2.3 is required for madcam-1 expression and homing of lymphocytes in spleen and mucosa-associated lymphoid tissue. Embo J 19, 2015-2023.

Panuncio, A. L., De La Pena, S., Gualco, G., and Reissenweber, N. (1999). Adrenergic innervation in reactive human lymph nodes. J Anat 194 (Pt 1), 143-146.

Pedersen, B. K. (2006). The anti-inflammatory effect of exercise: Its role in diabetes and cardiovascular disease control. Essays Biochem 42, 105-117.

Rebe, C., Raveneau, M., Chevriaux, A., Lakomy, D., Sberna, A. L., Costa, A., Bessede, G., Athias, A., Steinmetz, E., Lobaccaro, J. M., Alves, G., Menicacci, A., Vachenc, S., Solary, E., Gambert, P., and Masson, D. (2009). Induction of transglutaminase 2 by a liver x receptor/retinoic acid receptor alpha pathway increases the clearance of apoptotic cells by human macrophages. Circ Res 105, 393-401.

Scandella, E., Bolinger, B., Lattmann, E., Miller, S., Favre, S., Littman, D. R., Finke, D., Luther, S. A., Junt, T., and Ludewig, B. (2008). Restoration of lymphoid organ integrity through the interaction of lymphoid tissue-inducer cells with stroma of the t cell zone. Nat Immunol 9, 667-675.

Sixt, M., Kanazawa, N., Selg, M., Samson, T., Roos, G., Reinhardt, D. P., Pabst, R., Lutz, M. B., and Sorokin, L. (2005). The conduit system transports soluble antigens from the afferent lymph to resident dendritic cells in the t cell area of the lymph node. Immunity 22, 19-29.

Warnock, R. A., Askari, S., Butcher, E. C., and von Andrian, U. H. (1998). Molecular mechanisms of lymphocyte homing to peripheral lymph nodes. J Exp Med 187, 205-216.

Willard-Mack, C. L. (2006). Normal structure, function, and histology of lymph nodes. Toxicol Pathol 34, 409-424.

Woolf, E., Grigorova, I., Sagiv, A., Grabovsky, V., Feigelson, S. W., Shulman, Z., Hartmann, T., Sixt, M., Cyster, J. G., and Alon, R. (2007). Lymph node chemokines promote sustained t lymphocyte motility without triggering stable integrin adhesiveness in the absence of shear forces. Nat Immunol 8, 1076-1086.

Yamagata, T., Mathis, D., and Benoist, C. (2004). Self-reactivity in thymic double-positive cells commits cells to a cd8 alpha alpha lineage with characteristics of innate immune cells. Nat Immunol 5, 597-605.

Yip, L., Su, L., Sheng, D., Chang, P., Atkinson, M., Czesak, M., Albert, P. R., Collier, A. R., Turley, S. J., Fathman, C. G., and Creusot, R. J. (2009). Deaf1 isoforms control the expression of genes encoding peripheral tissue antigens in the pancreatic lymph nodes during type 1 diabetes. Nat Immunol 10, 1026-1033.

Yoneyama, H., Narumi, S., Zhang, Y., Murai, M., Baggiolini, M., Lanzavecchia, A., Ichida, T., Asakura, H., and Matsushima, K. (2002). Pivotal role of dendritic cell-derived cxcl10 in the retention of t helper cell 1 lymphocytes in secondary lymph nodes. J Exp Med 195, 1257-1266.

Zampetaki, A., Zhang, Z., Hu, Y., and Xu, Q. (2005). Biomechanical stress induces il-6 expression in smooth muscle cells via ras/rac1-p38 mapk-nf-kappab signaling pathways. Am J Physiol Heart Circ Physiol 288, H2946-2954.

We claim:

1. A method for suppressing an immune response comprising: administering to a subject in need of such treatment isolated lymphoid tissue-derived suppressive stromal cells (LSSC), wherein the LSSCs are fibroblastic reticular cells (FRCs) in an amount effective to suppress the immune response in the subject, and wherein the FRCs are passaged.

2. The method of claim 1, wherein the FRCs that are administered to the subject are ex vivo expanded cells.

3. The method of claim 1, wherein the FRCs that are administered to the subject are substantially free of non-LSSC.

4. The method of claim 1, wherein the FRCs that are administered to the subject are derived from lymph nodes, spleen, thymus, tonsils, adenoids, and/or Peyer's patches.

5. The method of claim 1, wherein the subject has an autoimmune or inflammatory disease.

6. The method of claim 1, wherein the FRCs are autologous or allogeneic or xenogeneic with respect to the subject.

7. The method of claim 1, wherein at least 0.1 million FRCs/kg are administered to the subject.

8. The method of claim 7, wherein at least 1 million FRCs/kg are administered to the subject.

9. The method claim 1, wherein the FRCs are administered such that the LSSC are on or in a two or three dimensional framework that is implanted into the subject.

10. The method of claim 5, wherein the autoimmune or inflammatory disease is selected from the group consisting of rheumatoid arthritis, multiple sclerosis, psoriasis, inflammatory bowel disease, graft-versus-host disease, and sepsis.

11. The method of claim 10, wherein the inflammatory bowel disease is colitis or Crohn's disease.

12. The method of claim 1, wherein the isolated FRCs co-express CD140a and PD-L2.

13. The method of claim 1, wherein the isolated FRCs co-express CD140a and LTBR.

14. The method of claim 1, wherein the isolated FRCs co-express CD140a, PD-L2 and LTBR.

15. The method of claim 1, wherein the isolated FRCs express at least one other lymphoid marker selected from the group consisting of PD-L1, Thy-1, MADCAM-1, IL-7R and ITGA7.

16. The method of claim 1, wherein the isolated FRCs express at least one factor selected from the group consisting of IL-6 and VEGF.

17. The method of claim 1, wherein the FRCs are isolated from a human.

18. The method of claim 1, wherein the FRCs suppress T cell proliferation in vitro.

19. The method of claim 1, wherein the isolated FRCs co-express CD140a, PD-L2 and LTBR, and wherein the subject has an autoimmune or inflammatory disease selected from the group consisting of rheumatoid arthritis, multiple sclerosis, psoriasis, inflammatory bowel disease, graft-versus-host disease, and sepsis.

20. The method of claim 1, wherein at least 1 million FRCs/kg are administered to the subject, and wherein the subject has an autoimmune or inflammatory disease selected from the group consisting of rheumatoid arthritis, multiple sclerosis, psoriasis, inflammatory bowel disease, graft-versus-host disease, and sepsis.

* * * * *

UNITED STATES PATENT AND TRADEMARK OFFICE
CERTIFICATE OF CORRECTION

PATENT NO. : 10,420,801 B2
APPLICATION NO. : 14/386535
DATED : September 24, 2019
INVENTOR(S) : Anne Fletcher et al.

Page 1 of 1

It is certified that error appears in the above-identified patent and that said Letters Patent is hereby corrected as shown below:

In the Specification

At Column 1, please replace the two "Federally Sponsored Research" paragraphs beginning on Line 15 and ending on Line 27, with the following amended "Federally Sponsored Research" paragraph:

FEDERALLY SPONSORED RESEARCH
This invention was made with government support under grant numbers DK074500, K01DK087770, and AI045757 awarded by the National Institutes of Health. The government has certain rights in the invention.

Signed and Sealed this
Eighteenth Day of February, 2020

Andrei Iancu
*Director of the United States Patent and Trademark Office*

UNITED STATES PATENT AND TRADEMARK OFFICE
CERTIFICATE OF CORRECTION

PATENT NO. : 10,420,801 B2
APPLICATION NO. : 14/386535
DATED : September 24, 2019
INVENTOR(S) : Anne Fletcher et al.

Page 1 of 1

It is certified that error appears in the above-identified patent and that said Letters Patent is hereby corrected as shown below:

In the Specification

At Column 1, please replace the "Federally Sponsored Research" paragraph beginning on Line 15 and ending on Line 20, with the following amended "Federally Sponsored Research" paragraph:

FEDERALLY SPONSORED RESEARCH
This invention was made with government support under grant numbers DK074500, AI045757 and DK087770 awarded by the National Institutes of Health. The government has certain rights in the invention.

Signed and Sealed this
Eighteenth Day of August, 2020

Andrei Iancu
*Director of the United States Patent and Trademark Office*